(12) United States Patent
Roush et al.

(10) Patent No.: US 7,943,642 B2
(45) Date of Patent: May 17, 2011

(54) INSECTICIDAL N,N-DI(HETEROARYLALKYL)AMINE DERIVATIVES

(75) Inventors: David M. Roush, Princeton, NJ (US); John F. Chiarello, Newton, PA (US); George Theodoridis, Princeton, NJ (US); Hongyan Qi, Plainsboro, NJ (US)

(73) Assignee: FMC Corporation, Philadelphia, PA (US)

( * ) Notice: Subject to any disclaimer, the term of this patent is extended or adjusted under 35 U.S.C. 154(b) by 658 days.

(21) Appl. No.: 11/577,664

(22) PCT Filed: Oct. 27, 2005

(86) PCT No.: PCT/US2005/038998
§ 371 (c)(1),
(2), (4) Date: May 28, 2008

(87) PCT Pub. No.: WO2006/050121
PCT Pub. Date: May 11, 2006

(65) Prior Publication Data
US 2008/0287506 A1 Nov. 20, 2008

Related U.S. Application Data

(60) Provisional application No. 60/622,740, filed on Oct. 28, 2004.

(51) Int. Cl.
*A01N 43/40* (2006.01)
*A01N 43/46* (2006.01)
*C07D 401/12* (2006.01)

(52) U.S. Cl. .................. 514/343; 546/276.4; 546/278.4; 546/278.7; 546/279.1

(58) Field of Classification Search ............... 546/276.4, 546/278.4, 278.7, 279.1; 514/343
See application file for complete search history.

(56) References Cited

U.S. PATENT DOCUMENTS
3,629,270 A * 12/1971 Gante ........................ 546/276.4
* cited by examiner

*Primary Examiner* — Patricia Morris

(57) ABSTRACT

Certain novel N,N-di(heteroarylalkyl)amine derivatives have provided unexpected insecticidal and acaricidal activity. These compounds are represented by formula (I): wherein Ar Ar$^1$, a, b, c, R, R$^d$, R$^e$, R$^f$, Rg, R$^h$, R', R$^3$ and R$^k$ are fully described herein. In addition, compositions comprising an insecticidally effective amount of at least one compound of formula I, and optionally, an effective amount of at least one of a second compound, with at least one insecticidally compatible carrier are also disclosed; along with methods of controlling insects comprising applying said compositions to a locus where insects are present or are expected to be present.

10 Claims, No Drawings

INSECTICIDAL N,N-DI(HETEROARYLALKYL)AMINE DERIVATIVES

This application claims the benefit of U.S. Provisional Application No. 60/622,740, filed Oct. 28, 2004.

FIELD OF THE INVENTION

The present invention generally relates to pesticidal compounds and their use in controlling insects and acarids. In particular, it pertains to compositions of pesticidal N,N-di(heteroarylalkyl)amine derivatives and agriculturally acceptable salts thereof, and methods for their use in controlling insects and acarids.

BACKGROUND OF THE INVENTION

It is well known that insects in general can cause significant damage, not only to crops grown in agriculture, but also, for example, to structures and turf where the damage is caused by soil-borne insects, such as termites and white grubs. Such damage may result in the loss of millions of dollars of value associated with a given crop, turf or structures. Although there are many orders of insects that can cause significant crop damage, insects, for example, of the order "Homoptera" are of major importance. The order Homoptera includes, for example, aphids, leafhoppers, cicadas, whiteflies, and mealybugs, to name a few. Homoptera have piercing/sucking mouthparts, enabling them to feed by withdrawing sap from vascular plants. Insect damage from Homoptera is manifested in several different ways, other than damage caused by direct feeding. For example, many species excrete honeydew, a sticky waste product that adheres to plants upon which the insect feeds and lives. Honeydew alone causes cosmetic injury to crop plants. Sooty molds will often grow on honeydew, making food products or ornamental plants look unappealing, thereby reducing their cosmetic and economic value. Some homoptera have toxic saliva that is injected into plants while they are feeding. The saliva can cause plant damage through disfigurement and in some instances plant death. Homoptera can also vector disease-causing pathogens. Unlike direct damage, it does not take a large number of disease-vectoring insects to cause considerable damage to crop plants.

Thus, there is a continuing demand for new insecticides, and for new acaricides that are safer, more effective, and less costly. Insecticides and acaricides are useful for controlling insects and acarids which may otherwise cause significant damage both above and below the soil level to crops such as wheat, corn, soybeans, potatoes, and cotton to name a few. For crop protection, insecticides and acaricides are desired which can control the insects and acarids without damaging the crops, and which have no deleterious effects to mammals and other living organisms.

A number of patents disclose some alkanediamine compounds that are reported to be insecticidally active. For example, U.S. Pat. No. 4,806,553 discloses certain insecticidal alkylenediamine compounds of the general formula I:

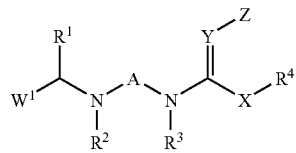

where
$W^1$ is a five- or six-membered heterocyclic group, which may be substituted, containing at least one heteroatom selected from —O—, —S—, and —N—;
$R^1$, $R^2$, and $R^3$ are hydrogen or alkyl;
$R^4$ is hydrogen, alkyl, aryl, aralkyl, alkoxy, dialkylamino, alkoxyalkyl, alkylthioalkyl, or —CH$_2$—W$^2$— in which $W^2$=$W^1$;
X is —S—, —NR$^5$, or a single bond, in which R$^5$ is hydrogen or alkyl, and in the case where X is —NR$^5$—, the group —NR$^4$R$^5$—, in the formula I may have the same meaning as the group

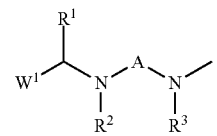

in formula I;
Y is —N—, or =CR$^6$—, in which R$^6$ is hydrogen, alkyl, aryl, acyl, alkoxycarbonyl, or cyano;
Z is cyano or nitro; and,
A is ethylene or trimethylene, which may be substituted with alkyl.

Published Japanese Patent Application 08269035A discloses certain tetrahydrofuran-3-ylmethyl derivatives of the general formula I:

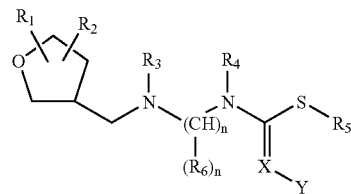

where
$R_1$ and $R_2$ are hydrogen, or optionally substituted $C_1$-$C_5$alkyl;
$R_3$-$R_5$ are hydrogen, optionally substituted $C_1$-$C_5$alkyl, optionally substituted $C_2$-$C_5$alkenyl, or optionally substituted $C_2$-$C_5$alkynyl; n is 2-5; $R_6$ is hydrogen or $C_1$-$C_3$alkyl; X is CH or N; Y is NO$_2$ or C≡N; and $R_3$ and $R_4$ together may form a ring.

U.S. Pat. No. 5,075,301 claims, inter alia, certain furan derivatives of the following general formula that are useful for the treatment of gastro-intestinal disorders:

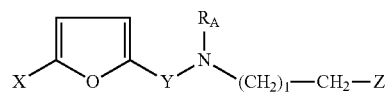

where
X is, among others, R$^1$CH$_2$— where R$^1$ is R$^2$R$^3$N—, where R$^2$ and R$^3$ are the same or different and each is hydrogen or lower alkyl;
Y is —CH$_2$— or —C(=O)—;
l is an integer of 1 through 3;
$R_A$ is hydrogen, lower alkyl, lower alkanoyl, or substituted or un-substituted aroyl;
Z is, among others,

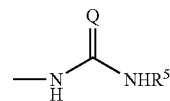

where

Q is oxygen or sulfur, $R^5$ is hydrogen, lower alkyl, or substituted or un-substituted aryl,

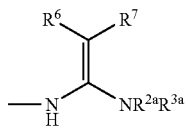

where $R^6$ and $R^7$ may be the same or different and each is hydrogen, cyano, lower alkoxycarbonyl, lower alkylsulfonyl, substituted or un-substituted arylsulfonyl, or nitro; provided that $R^6$ and $R^7$ cannot concurrently be hydrogen; $R^{2a}$ and $R^{3a}$ have the same meaning as $R^2$ and $R^3$ described above,

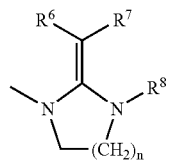

where $R^6$ and $R^7$ are as described above, $R^8$ is hydrogen or lower alkyl, and n is 1 or 2.

European Patent EP 0547451 B1 claims compounds of the following general formula that are useful as insecticides:

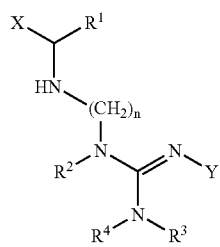

where

X represents 2-chloro-5-pyridyl or 2-chloro-5-thiazolyl;

$R^1$ represents hydrogen or $(C_1-C_4)$alkyl;

$R^2$ is hydrogen, $(C_1-C_4)$alkyl, $(C_3-C_4)$alkynyl, $(C_3-C_4)$alkenyl and 2-chloro-5-pyridyl;

$R^3$ and $R^4$ are selected from hydrogen, halogen, $(C_1-C_4)$alkyl, $(C_3-C_4)$alkynyl, $(C_3-C_4)$alkenyl and benzyl which may be substituted, or a group represented by $X-C(R^1)H-$ wherein X and $R^1$ are the same meaning as above;

N is an integer of 2 or 3, and

Y is $-NO_2$ or $-CN$.

U.S. Pat. No. 5,852,012 claims compositions of compounds and salts thereof of the following general formula that are useful as insecticides:

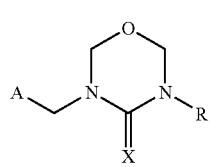

where

A is 2-chloropyrid-5-yl, 2-methylpyrid-5-yl, 1-oxido-3-pyridinio, 2-chloro-1-oxido-5-pyrinio, or 2-chlorothiazol-5-yl;

R is hydrogen; $(C_1-C_6)$alkyl, phenyl$(C_1-C_4)$alkyl, $(C_3-C_6)$cycloalkyl, $(C_2-C_6)$alkenyl or $(C_2-C_6)$alkynyl;

and

X is $N-NO_2$ or $N-CN$.

U.S. Pat. No. 5,580,889 discloses compounds of the following general formula that are useful as insecticides:

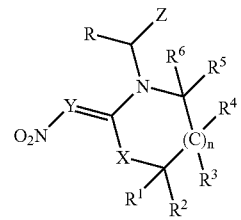

where n is 0 or 1;

$R^1, R^2, R^5$ and $R^6$ independently represent hydrogen or alkyl; $R^3$ and $R^4$ independently represent hydrogen, hydroxy or alkyl; where n is 1, then $R^2$ may form a single bond with $R^5$;

X represents $-S-$, $-O-$, $=N-R^7$ or $=CH-R^8$ wherein $R^7$ is, inter alia, hydrogen, halogen, alkyl, hydroxy, benzyl, benzyloxy, alkenylcarbonyl, benzyloxycarbonyl, mono- and dialkylaminocarbonyl, phenylaminocarbonyl, phenylsulfonylaminocarbonyl, alkylsulfonyl, and phenacyl; $R^8$ is hydrogen, alkyl, aryl and benzyl;

Y represents $-N-$ or $=C(-)-R^9$, wherein $R^9$ is, inter alia, hydrogen, halogen, hydroxy, alkyl, alkoxy, alkylthiocarbonyl, phenoxycarbonyl, phenylthiocarbonyl, benzoylaminocarbonyl, phenylsulfonylaminocarbonyl, alkylthio, alkylsulfonyl and phenylthio, phenylsulfonyl;

R represents hydrogen and alkyl;

and,

Z represents a 5- or 6-membered heterocyclic group containing at least one hetero atom selected from $-O-$, $-S-$ and $-N-$; which may be substituted There is no disclosure or suggestion in any of the above-referenced patents or patent application of the structures and insecticidal and acaricidal activity of the compounds of the present invention.

SUMMARY OF THE INVENTION

In accordance with the present invention, it has now been found that certain novel N,N-di(heteroarylalkyl)amine derivatives are surprisingly active in the control of insects and acarids when used in the insecticidal and acaricidal compositions and methods of this invention. The compounds of formula I are represented by the following general formula:

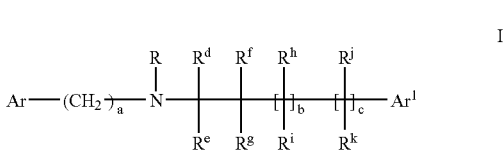

wherein
Ar is selected from

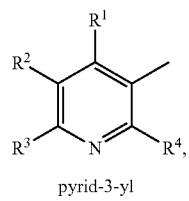

pyrid-3-yl

A

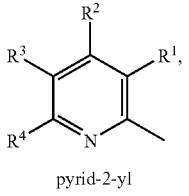

pyrid-2-yl

A1

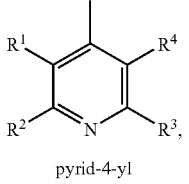

pyrid-4-yl

A2

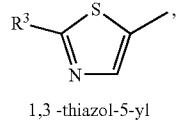

1,3-thiazol-5-yl

B

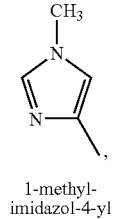

1-methyl-
imidazol-4-yl

C

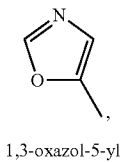

1,3-oxazol-5-yl

D

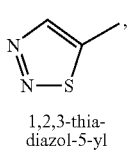

1,2,3-thia-
diazol-5-yl

E

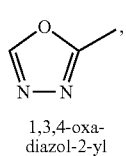

1,3,4-oxa-
diazol-2-yl

F

-continued

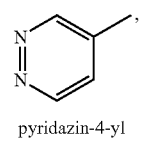

pyridazin-4-yl

G

2-chloro-
pyrimidin-5-yl

H

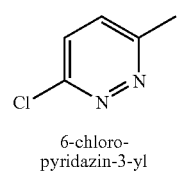

6-chloro-
pyridazin-3-yl

J

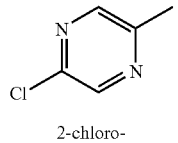

2-chloro-
pyrazin-5-yl

K

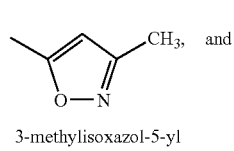 and 3-methylisoxazol-5-yl

L

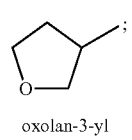;

oxolan-3-yl

M where
$R^1$, $R^2$, $R^3$, and $R^4$ are independently selected from hydrogen, halogen, alkyl, alkoxy, haloalkyl, haloalkoxy and haloalkylsulfonyl;

$Ar^1$ is selected from

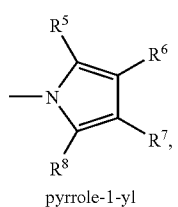

pyrrole-1-yl

N

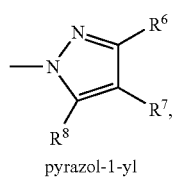

pyrazol-1-yl

O

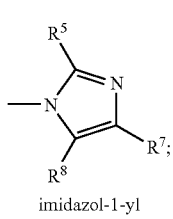

imidazol-1-yl a is an integer selected from 0 or 1;

R is selected from alkyl, haloalkyl, alkoxyalkyl, alkoxyalkoxyalkyl, cycloalkylalkyl, formyl, alkylcarbonyl, alkoxycarbonyl, alkylsulfonyl, dialkylphosphonato, oxolan-3-ylmethyl, 2H-3,4,5,6-tetrahydropyran-2-ylmethyl, thien-3-ylmethyl, furan-2-ylmethyl, furan-3-ylmethyl, 1,3-oxazol-2-ylmethyl, benzo[b]furan-2-ylmethyl, —(CH$_2$)$_m$C≡N,

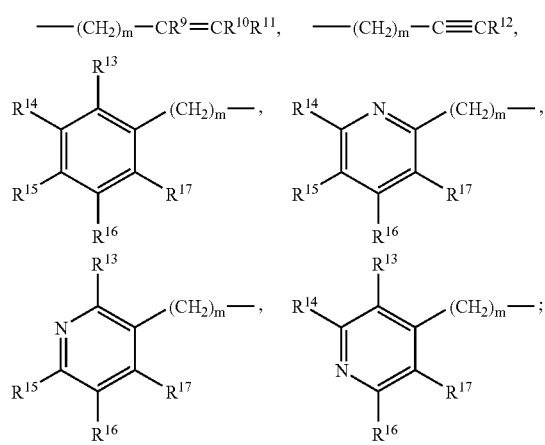

2-R$^{18}$-1,3-thiazol-4-ylmethyl and 5-R$^{18}$-1,2,4-oxadiazol-3-ylmethyl, where m is an integer selected from 1 or 2;

R$^9$, R$^{10}$ and R$^{11}$ are independently selected from hydrogen, halogen, alkyl and aryl;

R$^{12}$ is selected from hydrogen, alkyl,

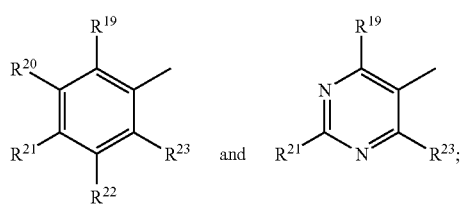

where

R$^{19}$, R$^{20}$, R$^{21}$, R$^{22}$, and R$^{23}$ are independently selected from hydrogen, halogen, alkyl, haloalkyl, alkoxy, and haloalkoxy;

R$^{13}$, R$^{14}$, R$^{15}$, R$^{16}$, and R$^{17}$ are independently selected from hydrogen, halogen, alkyl, haloalkyl, alkoxy, haloalkoxy, alkoxyiminoalkyl, cyano, nitro, 2-alkyl-2H-tetrazol-5-yl, aryl, and aryloxy;

and,

R$^{18}$ is selected from halogen, alkyl, aryl, and heteroaryl, wherein aryl and heteroaryl are optionally substituted with at least one of halogen, alkyl, haloalkyl, alkoxy, and haloalkoxy;

R$^d$, R$^e$, R$^f$ and R$^g$ are independently selected from hydrogen and alkyl;

b and c are integers independently selected from 0 or 1;

R$^h$, R$^i$, R$^j$ and R$^k$ are independently selected from hydrogen and alkyl;

R$^5$ and R$^6$ are independently selected from hydrogen, halogen, nitro, alkyl, alkoxy, alkenyloxy, alkynyloxy, haloalkyl, haloalkoxy, alkylthio, alkenylthio, alkynylthio, haloalkylthio, alkylsulfoxy, alkylsulfinyl, alkylsulfonyl, haloalkylsulfonyl, alkylamino, dialkylamino, hydroxycarbonyl and alkoxycarbonyl;

R$^7$ is selected from halogen, trifluoromethyl, cyano, nitro, formyl, hydroxycarbonyl, alkoxycarbonyl, aryloxycarbonyl, alkoxysulfonyl and alkoxysulfinyl;

R$^8$ is selected from halogen, nitro, alkoxy, alkenyloxy, alkynyloxy, haloalkoxy, alkylthio, alkenylthio, alkynylthio, haloalkylthio, alkylsulfoxy, alkylsulfinyl, alkylsulfonyl, haloalkylsulfonyl, alkylamino and dialkylamino;

and agriculturally acceptable salts thereof.

The present invention is also directed to compositions containing an insecticidally effective amount of at least one of a compound of formula I, and optionally, an effective amount of at least one of a second compound, with at least one insecticidally compatible carrier.

The present invention is also directed to methods of controlling insects, where control is desired, which comprise applying an insecticidally effective amount of the above composition to the locus of crops, or other areas where insects are present or are expected to be present.

DETAILED DESCRIPTION OF THE INVENTION

The present invention generally relates to certain new and useful compounds, namely novel N,N-di(heteroarylalkyl) amine derivatives (hereinafter termed "compounds of formula I") as depicted in formula I:

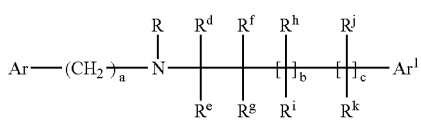

wherein

Ar is selected from

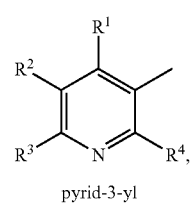

pyrid-3-yl

-continued

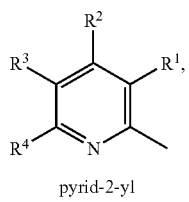
pyrid-2-yl

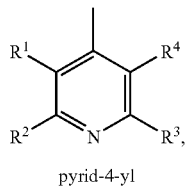
pyrid-4-yl

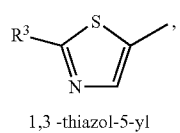
1,3-thiazol-5-yl

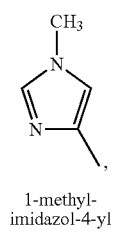
1-methyl-imidazol-4-yl

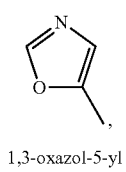
1,3-oxazol-5-yl

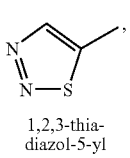
1,2,3-thia-diazol-5-yl

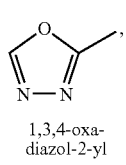
1,3,4-oxa-diazol-2-yl

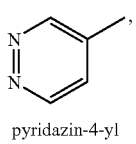
pyridazin-4-yl

2-chloro-pyrimidin-5-yl

-continued

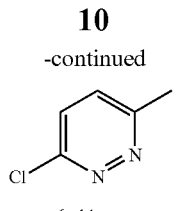
6-chloro-pyridazin-3-yl

2-chloro-pyrazin-5-yl

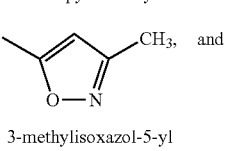
3-methylisoxazol-5-yl

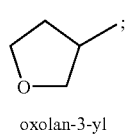
oxolan-3-yl where
R¹, R², R³, and R⁴ are independently selected from hydrogen, halogen, alkyl, alkoxy, haloalkyl, haloalkoxy and haloalkylsulfonyl;
Ar¹ is selected from

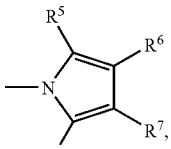
pyrrole-1-yl

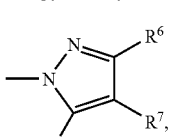
pyrazol-1-yl

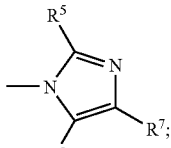
imidazol-1-yl a is an integer selected from 0 or 1;
R is selected from alkyl, haloalkyl, alkoxyalkyl, alkoxyalkoxyalkyl, cycloalkylalkyl, formyl, alkylcarbonyl, alkoxycarbonyl, alkylsulfonyl, dialkylphosphonato, oxolan-3-ylmethyl, 2H-3,4,5,6-tetrahydropyran-2-ylmethyl, thien-3-ylmethyl, furan-2-ylmethyl, furan-3-ylmethyl, 1,3-oxazol-2-ylmethyl, benzo[b]furan-2-ylmethyl, —(CH₂)ₘC≡N, $-(CH_2)_m-CR^9=CR^{10}R^{11}$, $-(CH_2)_m-C\equiv CR^{12}$,

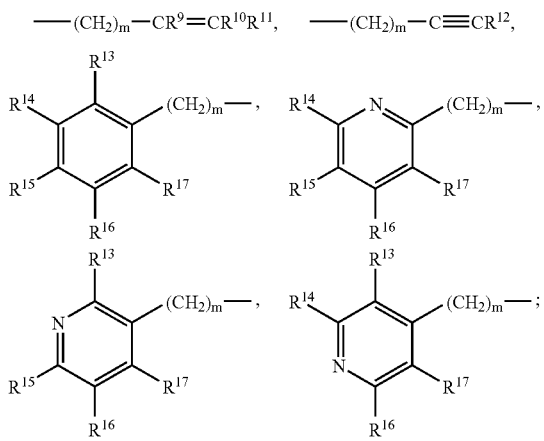

2-$R^{18}$-1,3-thiazol-4-ylmethyl and 5-$R^8$-1,2,4-oxadiazol-3-ylmethyl, where m is an integer selected from 1 or 2;

$R^9$, $R^{10}$ and $R^{11}$ are independently selected from hydrogen, halogen, alkyl and aryl;

$R^{12}$ is selected from hydrogen, alkyl,

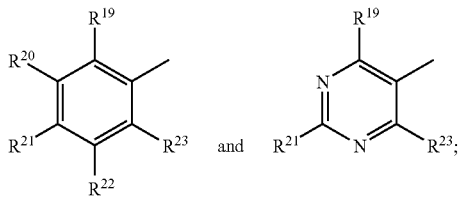

where $R^{19}$, $R^{20}$, $R^{21}$, $R^{22}$, and $R^{23}$ are independently selected from hydrogen, halogen, alkyl, haloalkyl, alkoxy, and haloalkoxy;

$R^{13}$, $R^{14}$, $R^{15}$, $R^{16}$, and $R^{17}$ are independently selected from hydrogen, halogen, alkyl, haloalkyl, alkoxy, haloalkoxy, alkoxyiminoalkyl, cyano, nitro, 2-alkyl-2H-tetrazol-5-yl, aryl, and aryloxy;

and, $R^{18}$ is selected from halogen, alkyl, aryl, and heteroaryl, wherein aryl and heteroaryl are optionally substituted with at least one of halogen, alkyl, haloalkyl, alkoxy, and haloalkoxy;

$R^d$, $R^e$, $R^f$ and $R^g$ are independently selected from hydrogen and alkyl;

b and c are integers independently selected from 0 or 1;

$R^h$, $R^i$, $R^j$ and $R^k$ are independently selected from hydrogen and alkyl;

$R^5$ and $R^6$ are independently selected from hydrogen, halogen, nitro, alkyl, alkoxy, alkenyloxy, alkynyloxy, haloalkyl, haloalkoxy, alkylthio, alkenylthio, alkynylthio, haloalkylthio, alkylsulfoxy, alkylsulfinyl, alkylsulfonyl, haloalkylsulfonyl, alkylamino, dialkylamino, hydroxycarbonyl and alkoxycarbonyl;

$R^7$ is selected from halogen, trifluoromethyl, cyano, nitro, formyl, hydroxycarbonyl, alkoxycarbonyl, aryloxycarbonyl, alkoxysulfonyl and alkoxysulfinyl;

$R^8$ is selected from halogen, nitro, alkoxy, alkenyloxy, alkynyloxy, haloalkoxy, alkylthio, alkenylthio, alkynylthio, haloalkylthio, alkylsulfoxy, alkylsulfinyl, alkylsulfonyl, haloalkylsulfonyl, alkylamino and dialkylamino;

and agriculturally acceptable salts thereof.

Preferred compounds of the present invention as set forth above are those compounds of formula I where b and c are each 0, and more preferred are those where Ar is selected from pyrid-3-yl (A), 1,3-thiazol-5-yl (B), or oxolan-3-yl (M) and $Ar^1$ is pyrrole-1-yl (N). Yet more preferred compounds of the present invention are those where $R^7$ is nitro.

In addition, in certain cases the compounds of the present invention may possess asymmetric centers, which can give rise to optical enantiomorphs and diastereomers. The compounds may exist in two or more forms, i.e., polymorphs, which are significantly different in physical and chemical properties. The compounds of the present invention may also exist as tautomers, in which migration of a hydrogen atom within the molecule results in two or more structures, which are in equilibrium. The compounds of the present invention may also possess acidic or basic moieties, which may allow for the formation of agriculturally acceptable salts or agriculturally acceptable metal complexes.

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

The methods of the present invention are predicated on causing an insecticidally effective amount of a compound of formula I to be present within insects in order to kill or control the insects. Preferred insecticidally effective amounts are those that are sufficient to kill the insect. It is within the scope of the present invention to cause a compound of formula I to be present within insects by contacting the insects with a derivative of that compound, which derivative is converted within the insect to a compound of formula I. This invention includes the use of such compounds, which can be referred to as pro-insecticides.

Another aspect of the present invention relates to compositions containing an insecticidally effective amount of at least one compound of formula I with at least one insecticidally compatible carrier therefor.

Another aspect of the present invention relates to compositions containing an insecticidally effective amount of at least one compound of formula I, and an effective amount of at least one additional compound, with at least one insecticidally compatible carrier therefor.

Another aspect of the present invention relates to methods of controlling insects by applying an insecticidally effective amount of a composition set forth above to a locus of crops such as, without limitation, cereals, cotton, vegetables, and fruits, or other areas where insects are present or are expected to be present.

The present invention also includes the use of the compounds and compositions set forth herein for control of non-agricultural insect species, for example, dry wood termites and subterranean termites; as well as for use as pharmaceutical agents and compositions thereof. In the field of veterinary medicine, the compounds of the present invention are expected to be effective against certain endo- and ecto-parasites, such as insects and worms, which prey on animals. Examples of such animal parasites include, without limitation, *Gastrophilus* spp., *Stomoxys* spp., *Trichodectes* spp., *Rhodnius* spp., *Ctenocephalides canis*, and other species.

As used in this specification and unless otherwise indicated the substituent terms "alkyl" and "alkoxy", used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. The term "alkenyl" and "alkynyl" used alone or as part of a larger moiety, includes straight or branched chains of at least two carbon atoms containing at least one carbon-carbon double bond or triple bond, and preferably up to 12 carbon atoms, more preferably up to ten carbon atoms, most preferably up to seven carbon atoms. The term "aryl" refers to an aromatic ring structure, including fused rings, having four to ten carbon atoms, for example, phenyl or naphthyl. The term "heteroaryl" refers to an aromatic ring structure, including fused rings, in which at least one of the atoms is other than carbon, for example, without limitation, sulfur, oxygen, or nitrogen. The term "GC analysis" refers to gas chromatographic analysis of, for example, a chemical reaction mixture. The term "DMF" refers to N,N-dimethylformamide. The term "THF" refers to tetrahydrofuran. The term "halogen" or "halo" refers to fluorine, bromine, iodine, or chlorine. The term "ambient temperature" or "room temperature" often abbreviated as "RT", for example, in reference to a chemical reaction mixture temperature, refers to a temperature in the range of 20° C. to 30° C. The term "insecticidal" or "acaricidal", "insecticide" or "acaricide" refers to a compound of the present invention, either alone or in admixture with at least one of a second compound, or with at least one compatible carrier, which causes the destruction or the inhibition of action of insects or acarids.

The novel compounds of formula I can be synthesized by methods that are individually known to one skilled in the art from intermediate compounds readily available in commerce.

Scheme 1 below illustrates a general procedure for synthesizing N,N-di(heteroarylalkyl)amine derivatives of formula I, inter alia, where, for example Ar is A (pyrid-3-yl), $R^1$, $R^2$ and $R^4$ are hydrogen, and $R^3$ is chlorine; a is 1; b and c are 0; and $R^a$, $R^b$, $R^c$ and $R^d$ are hydrogen:

Scheme 1

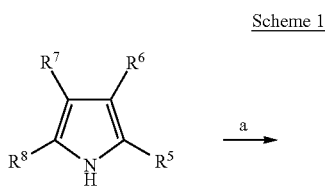

where $R^5$ and $R^7$ are hydrogen; $R^6$ is $NO_2$ and $R^8$ is $CO_2C_2H_5$
Commerically available

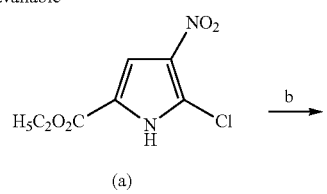

(a)

where $R^5$ is, for example, chlorine

-continued

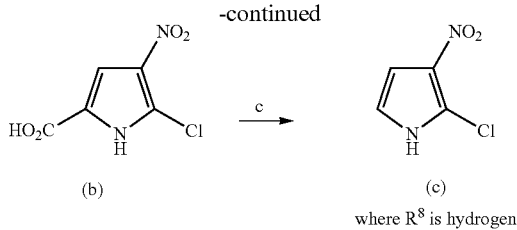

where $R^8$ is hydrogen

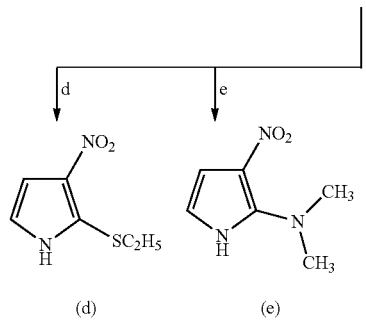

where $R^5$ is, for example, $SC_2H_5$     where $R^5$ is, for example, $N(CH_3)_2$ a) $SO_2Cl_2/HOAc/80°$ C. b) aq 10% $NaOH/CH_3OH/80°$ C. c) Δ/ethylene glycol d) $HSC_2H_5/N[C_2H_5][CH(CH_3)_2]_2/$ 100-175° C. (microwave) e) $HN(CH_3)_2/100°$ C. (microwave)

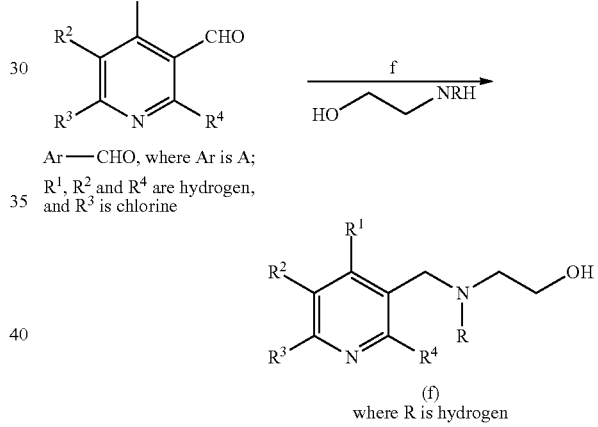

Ar—CHO, where Ar is A;
$R^1$, $R^2$ and $R^4$ are hydrogen, and $R^3$ is chlorine (f)
where R is hydrogen f) $NaBH(OAc)_3/ClC_2H_4Cl/MgSO_4/RT$

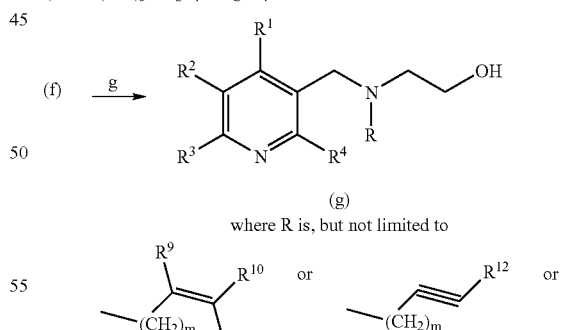

(g)
where R is, but not limited to

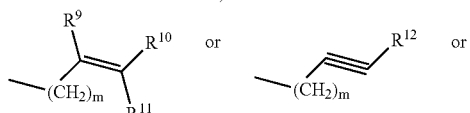

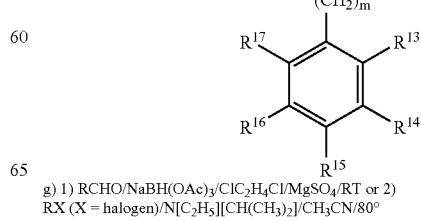

g) 1) $RCHO/NaBH(OAc)_3/ClC_2H_4Cl/MgSO_4/RT$ or 2) RX (X = halogen)/$N[C_2H_5][CH(CH_3)_2]/CH_3CN/80°$

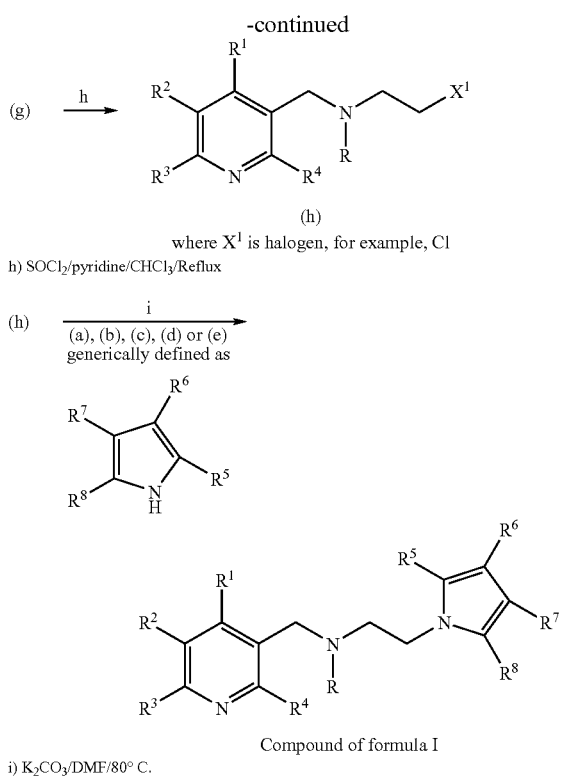

where $X^1$ is halogen, for example, Cl h) $SOCl_2$/pyridine/$CHCl_3$/Reflux i) $K_2CO_3$/DMF/80° C.

As depicted in Scheme 1, in one set of reactions, five-membered heterocyclic intermediates (a), (b), (c), (d) and (e) were prepared by methods known to those skilled in the art (Journal of Antibiotics 1569, 34(12) 1981). For example, the known compound ethyl 4-nitropyrrole-2-carboxylate was treated with sulfuryl chloride in an appropriate acidic solvent, yielding the chlorinated intermediate (a), which was in turn reduced under strong basic conditions, affording the corresponding intermediate (b), for example 5-chloro-4-nitropyrrole-2-carboxylic acid. Intermediate (b) was then heated at high temperature (about 190° C.) in an appropriate solvent, yielding the corresponding decarboxylated intermediate (c), for example 2-chloro-3-nitropyrrole. Intermediate (c) was either used directly to prepare compounds of formula I or was reacted to prepare other intermediates with which to prepare compounds of formula I. For example, Intermediate (c) was treated 1) with ethylmercaptan under basic conditions, providing intermediate (d), or 2) with dimethylamine, providing intermediate (e).

In a second set of reactions, an appropriate aldehyde, for example (6-chloro-3-pyridyl)formaldehyde, was reacted with an aminoalkanol of appropriate alkyl chain length, such as 2-aminoethan-1-ol, affording the corresponding N-(substituted amino)alkanol derivative, intermediate (f). Intermediate (f), for example 2-{[(6-chloro-3-pyridyl)methyl]amino}ethan-1-ol, was in turn reacted either 1) with an appropriate second aldehyde or 2) with an appropriate halide, affording the corresponding N,N-(disubstituted amino)alkanol derivative, intermediate (g), Intermediate (g) was then halogenated with, for example thionyl chloride, providing intermediate (h), for example [(6-chloro(3-pyridyl))methyl](2-chloroethyl)[(4-methoxyphenyl)methyl]amine.

The intermediates prepared in the sets of reactions outlined above were in turn reacted together under basic conditions in an appropriate solvent at mild temperature (about 80° C.). For example intermediate (c), 2-chloro-3-nitropyrrole, was reacted with intermediate (h), [(6-chloro(3-pyridyl))methyl](2-chloroethyl)[(4-methoxyphenyl)methyl]amine, providing Compound 28, a compound of formula I. Examples 1 through 3 set forth below provide detailed methods by which the compounds of formula I were prepared.

One skilled in the art will, of course, recognize that the formulation and mode of application of a toxicant may affect the activity of the material in a given application. Thus, for agricultural use the present insecticidal compounds may be formulated as a granule of relatively large particle size (for example, 8/16 or 4/8 US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isphorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal and acaricidal compounds of this invention may be formulated and/or applied with one or more additional compounds. Such combinations may provide certain advantages, such as, without limitation, exhibiting synergistic effects for greater control of insect pests, reducing rates of application of insecticide thereby minimizing any impact to the environment and to worker safety, controlling a broader spectrum of insect pests, safening of crop plants to phytotoxicity, and improving tolerance by non-pest species, such as mammals and fish.

Additional compounds include, without limitation, other pesticides, plant growth regulators, fertilizers, soil conditioners, or other agricultural chemicals. In applying an active compound of this invention, whether formulated alone or with other agricultural chemicals, an effective amount and concentration of the active compound is of course employed; the amount may vary in the range of, e.g. about 0.001 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with one or more additional compounds, e.g., with other pesticides such as herbicides, the herbicides include, without limitation, for example: N-(phosphonomethyl)glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4-chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)$_2$-[4,5-dihydro-4-methyl-4-(1-methylethyl)-5-oxo-1H-imidazol-2-yl]-5-methylbenzoic acid ("imazamethabenz"), (+/−)-2-[4,5-dihydro-4-methyl-4-(1-methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4-chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfonamide (achlorsulfuron"), 2-[[[[[(4,6-dimethoxy-2-pyrimidinyl)amino]carbonyl]amino]sulfonyl]methyl]benzoic acid ("bensulfuron"), 2-[[[[(4,6-dimethoxy-2-pyrimidinyl)amino]carbonyl]amino]sulfonyl]-1-methyl-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N[[(4-methoxy-6-methyl-1,3,5-triazin-2-yl)amino]carbonyl]benzenesulfonamide ("triasulfuron"); 2-(4-aryloxyphenoxy)alkanoic acids such as (+/−)-2[4-[(6-chloro-2-benzoxazolyl)oxy]phenoxy]-propanoic acid (fenoxaprop"), (+/−)-2-[4[[5-(trifluoromethyl)-2-pyridinyl]oxy]-phenoxy]propanoic acid ("fluazifop"), (+/−)-2-[4-(6-chloro-2-quinoxalinyl)oxy]-phenoxy]propanoic acid ("quizalofop"), and (+/−)-2-[(2,4-dichlorophenoxy)phenoxy]propanoic acid ("diclofop"); benzothiadiazinones such as 3-(1-methylethyl)-1H-1,2,3-benzothiadiazin-4(3H)-one-2,2-dioxide ("bentazone"); 2-chloroacetanilides such as N-(butoxymethyl)-2-chloro-N-(2,6-diethylphenyl)acetamide ("butachlor"), 2-chloro-N-(2-ethyl-6-methylphenyl)-N-(2-methoxy-1-methylethyl)acetamide ("metolachlor"), 2-chloro-N-(ethoxymethyl)-N-(2-ethyl-6-methylphenyl)acetamide ("acetochlor"), and (RS)-2-chloro-N-(2,4-dimethyl-3-thienyl)-N-(2-methoxy-1-methylethyl)acetamide ("dimethenamide"); arenecarboxylic acids such as 3,6-dichloro-2-methoxybenzoic acid ("dicamba"); pyridyloxyacetic acids such as [(4-amino-3,5-dichloro-6-fluoro-2-pyridinyl)oxy]acetic acid ("fluoroxypyr"); aryl triazolinones such as 1H-1,2,4-triazol-1-carboxamide ("amicarbazone"), 1,2,4-triazolo[4,3-a]pyridine-3(2H)-one ("azafenidin"), N-(2,4-dichloro-5-[4-(difluoromentyl)-4,5-dihydro-3-methyl-5-oxo-1H-1,2,4-triazol-1-yl]phenyl)methanesulfonamide ("sulfentrazone") and ethyl α,2-dichloro-5-[4-(difluoromethyl)-4,5-dihydro-3-methyl-5-oxo-1H-1,2,4-triazol-1-yl]-4-fluorobenzenepropanoate ("carfentrazone-ethyl"); isoxazolidinones such as 2[(2-chlorophenyl)methyl]-4,4-dimethyl-3-isoxazoline ("clomazone"); and other herbicides.

When the active insecticidal compounds of the present invention are used in combination with one or more additional compounds, e.g., with other pesticides such as other insecticides, the other insecticides include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, cypermethrin, alpha-cypermethrin, beta-cypermethrin, zeta-cypermethrin, bifenthrin, resolved cyhalothrin, etofenprox, esfenvalerate, tralomehtrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, spinosad, and imidacloprid.

When the active insecticidal compounds of the present invention are used in combination with one or more additional compounds, e.g., with other pesticides such as fungicides, the fungicides include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with one or more additional compounds, e.g., with other pesticides such as nematicides, the nematicides include, for example: carbofuran, carbosulfan, turbufos, aldecarb, ethoprop, fenamphos, oxamyl, isazofos, cadusafos, and other nematicides.

When the active insecticidal compounds of the present invention are used in combination with one or more additional compounds, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobium*, and soil-borne cyanobacteria.

Fertilizers are plant food supplements, which commonly contain nitrogen, phosphorus, and potassium. When the active insecticidal compounds of the present invention are used in combination with one or more of second compounds, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The following examples further illustrate the present invention, but, of course, should not be construed as in any way limiting its scope. The examples are organized to present protocols for the synthesis of the compounds of formula I of the present invention, set forth a list of such synthesized species, and set forth certain biological data indicating the efficacy of such compounds.

EXAMPLE 1

This Example Illustrates One Protocol for the Preparation of [(6-chloro(3-pyridyl))methyl][2-(2-chloro-3-nitropyrrolyl)ethyl][4-methoxyphenyl)methyl]amine (Compound 188)

Step A Synthesis of 2-{[(6-chloro-3-pyridyl)methyl]amino}ethan-1-ol as an intermediate A mixture of 20 grams (0.142 mole) of (6-chloro-3-pyridyl)formaldehyde and 31.3 grams (0.284 mole) of magnesium sulfate in 800 mL of 1,2-dichloroethane was stirred and 13.0 grams (0.213 mole) of 2-aminoethan-1-ol was added. Upon completion of addition, the reaction mixture was stirred for six hours, and 45.1 grams (0.213 mole) of sodium triacetoxyborohydride was added. Following the addition, the reaction mixture was stirred for about 72 hours, and then it was diluted with 250 mL of an aqueous solution comprised of 125 mL of an aqueous solution saturated with sodium chloride and 125 mL of water. The organic layer was separated and the aqueous layer was washed with ten 100 mL portions of 25% isopropanol in methylene chloride. The combined washes were dried with sodium sulfate and concentrated under reduced pressure to a residue. The residue was purified with column chromatography on silica gel. Elution was accomplished using mixtures of 5% methanol and 20% methanol in methylene chloride as eluants. The appropriate fractions were combined and concentrated under reduced pressure, yielding 9.8 grams of the subject compound. The NMR spectrum was consistent with the proposed structure.

Step B Synthesis of 2-{[(6-chloro(3-pyridyl)methyl][(4-methoxyphenyl)methyl]amino}ethan-1-ol as an intermediate This compound was prepared in a manner analogous to that of Step A of Example 1, using 4.9 grams (0.026 mole) of 2-{[(6-chloro-3-pyridyl)methyl]amino}ethan-1-ol, 3.6 grams (0.026 mole) of 4-methoxybenzaldehyde, 8.3 grams (0.039 mole) of sodium triacetoxyborohydride and 5.8 grams (0.052 mole) of magnesium sulfate in 200 mL of 1,2-dichloroethane. The crude product was purified with column chromatography on silica gel. Elution was accomplished using 100% methylene chloride and 100% diethyl ether as eluants. The appropriate fractions were combined and concentrated under reduced pressure, yielding 9.3 grams of the subject compound. The NMR spectrum was consistent with the proposed structure.

Step C Synthesis of [(6-chloro(3-pyridyl))methyl](2-chloroethyl)[(4-methoxyphenyl)methyl]amine as an intermediate A solution of 6.8 grams (0.022 mole) of 2-{[(6-chloro(3-pyridyl)methyl][(4-methoxyphenyl)methyl]amino}ethan-1-ol in 200 mL of chloroform was stirred and a solution of 2.9 grams (0.024 mole) of thionyl chloride in 50 mL of chloroform was added dropwise. Upon completion of addition, the reaction mixture was stirred at ambient temperature during one hour, and then it was warmed to reflux where it stirred for 2.5 hours. After this time the reaction mixture was cooled to room temperature and was slowly poured into a solution of 100 mL of aqueous 5% sodium carbonate. The organic layer was separated and dried with sodium sulfate, filtered, and the filtrate was concentrated under reduced pressure to a residue. The residue was purified with column chromatography on silica gel. Elution was accomplished using 2% diethyl ether in methylene chloride as an eluant. The appropriate fractions were combined and concentrated under reduced pressure, yielding 6.4 grams of the subject compound. The NMR spectrum was consistent with the proposed structure.

Step D Synthesis of ethyl 5-chloro-4-nitropyrrole-2-carboxylate as an intermediate A stirred solution of 5.0 grams (0.0272 mole) of ethyl 4-nitropyrrole-2-carboxylate (commercially available) and 5.5 grams (0.0408 mole) of sulfuryl chloride in 150 mL of acetic acid was warmed to 80° C., where it was maintained during a 3.5-hour period. After this time the reaction mixture was allowed to cool to ambient temperature as it stirred during an 18-hour period. The reaction mixture was concentrated under reduced pressure to a residue, and the residue was stirred with 250 mL of ethyl acetate and 100 mL of water. The organic layer was separated and washed with 150 mL of a solution of 75 mL of water and 75 mL of an aqueous solution saturated with sodium bicarbonate. The organic layer was dried with sodium sulfate, filtered, and the filtrate was concentrated under reduced pressure to a residue. The residue was purified with column chromatography on silica gel. Elution was accomplished using mixtures of 15% to 20% diethyl ether in hexane as eluants. The appropriate fractions were combined and concentrated under reduced pressure, yielding 2.1 grams of the subject compound. The NMR spectrum was consistent with the proposed structure.

Step E Synthesis of 5-chloro-4-nitropyrrole-2-carboxylic acid as an intermediate A stirred solution of 0.40 gram (0.0018 mole) of ethyl 5-chloro-4-nitropyrrole-2-carboxylate and 10 mL (excess) of an aqueous solution of 10% sodium hydroxide in 25 mL of methanol was warmed to 80° C. where it was maintained during a 1.5-hour period. After this time the reaction mixture was cooled and the methanol was removed under reduced pressure. The concentrate was diluted with 50 mL of water and 50 mL of ethyl acetate, and acidified to a pH of about 2.0. The organic layer was separated, dried with sodium sulfate, filtered, and the filtrate was concentrated under reduced pressure to a residue. The yield of the subject compound was 0.34 gram. The NMR spectrum was consistent with the proposed structure.

Step F Synthesis of 2-chloro-3-nitropyrrole as an intermediate

A stirred solution of 0.34 gram (0.0018 mole) of 5-chloro-4-nitropyrrole-2-carboxylic acid in about 5 mL of ethylene glycol was heated to 190° C. where it was maintained during a one-hour period. After this time the reaction mixture was cooled and diluted with 20 mL of water and 25 mL of ethyl acetate. The organic layer was separated and washed with 25 mL of a solution of 12.5 mL of water and 12.5 mL of an aqueous solution saturated with sodium bicarbonate. The organic layer was then dried with sodium sulfate, filtered, and the filtrate was concentrated under reduced pressure to a residue. The residue was purified with column chromatography on silica gel. Elution was accomplished using diethyl ether as an eluant. The appropriate fractions were combined and concentrated under reduced pressure, yielding 0.21 gram of the subject compound. The NMR spectrum was consistent with the proposed structure.

Step G Synthesis of Compound 188

A stirred solution of 0.38 gram (0.00115 mole) of [(6-chloro(3-pyridyl))methyl](2-chloroethyl)[(4-methoxyphenyl)methyl]amine (prepared in Steps A-C of the present Example), 0.15 gram (0.00100 mole) of 2-chloro-3-nitropyrrole and 0.36 gram (00260 mole) of potassium carbonate in 20 mL of DMF was warmed to 80° C. where it stirred for three hours. After this time, the reaction mixture was cooled and concentrated under reduced pressure to a residue. The residue was shaken with 25 mL of water and 25 mL of ethyl acetate. The organic layer was separated and dried with sodium sulfate. The mixture was filtered, the filtrate was absorbed onto silica gel and subjected to column chromatography. Elution was accomplished using methylene chloride as an eluant. The appropriate fractions were combined and concentrated under reduced pressure, yielding 0.20 gram of Compound 188. The NMR spectrum was consistent with the proposed structure.

EXAMPLE 2

This Example Illustrates One Protocol for the Preparation of 2-{[(6-chloro(3-pyridyl))methyl][2-(2-ethylthio-3-nitropyrrolyl)ethyl]amino}ethanenitrile (Compound I)

Step A Synthesis of 2-{[(6-chloro(3-pyridyl)methyl](2-hydroxyethylamino}-ethanenitrile as an intermediate A solution of 7.5 grams (0.0402 mole) of 2-{[(6-chloro-3-pyridyl)methyl]amino}ethan-1-ol (prepared in Step A of Example 1) in 100 mL of acetonitrile was stirred and 13.0 grams (0.1000 mole) of ethyldiisopropylamine was added, followed by 7.4 grams (0.0442 mole) of iodoacetonitrile. Upon completion of addition the reaction mixture was warmed to 80° C. where it was maintained for a six-hour period. After this time the reaction mixture was allowed to cool to ambient temperature as it stirred during an 18-hour period. The reaction mixture was then concentrated under reduced pressure to a residue. The residue was dissolved in methylene chloride and washed with one 50 mL portion of aqueous 5% sodium carbonate and with one portion of water. The organic layer was dried with sodium sulfate, filtered, and the filtrate was concentrated under reduced pressure to a residue. The residue was purified with column chromatography on silica gel. Elution was accomplished using 1% and 2%

23 mixtures of methanol in methylene chloride as eluants. The appropriate fractions were combined and concentrated under reduced pressure, yielding 6.9 grams of the subject compound. The NMR spectrum was consistent with the proposed structure.

Step B Synthesis of 2-{[(6-chloro(3-pyridyl)methyl](2-chloroethylamino}-ethanenitrile as an intermediate This compound was prepared in a manner analogous to that set forth in Step C of Example 1, using 5.7 grams (0.0255 mole) of 2-{[(6-chloro(3-pyridyl)methyl](2-hydroxyethylamino}ethanenitrile 3.2 grams (0.0268 mole) of thionyl chloride and one drop (catalyst) of pyridine in 50 mL of chloroform. The yield of the subject compound was 6.0 grams. The NMR spectrum was consistent with the proposed structure.

Step C Synthesis of 2-ethylthio-3-nitropyrrole as an intermediate

Using a microwave chemical reactor (CEM Explorer Microwave System manufactured by CEM Corporation, 3100 Smith Farm Road, Matthews N.C., 28106-0200), 0.1 gram (0.70 millimole) of 2-chloro-3-nitropyrrole (prepared in Steps D-F of Example 1), 0.5 mL (excess) of ethylmercaptan and 0.2 mL of ethyldiisopropylamine (excess) in 5 mL of acetonitrile were placed in an appropriate 10 mL vile. The vile was sealed and placed in the reaction chamber of the microwave chemical reactor. At 150 watts of power, the microwave reactor was brought to 100° C. during a five-minute period, where it was maintained for a 30-minute period. In a like manner the reactor was brought to 150° C. where it was maintained for a 30-minute period, and finally to 175° C. where it was maintained for a 30-minute period, after which time the reaction was considered to be complete. Upon completion of the reaction the microwave reactor was cooled, and the vile containing the reaction mixture was removed from the reactor and absorbed onto silica gel. The silica gel-reaction mixture combination was then subjected to column chromatography. Elution was accomplished using 33% diethyl ether in hexane. The appropriate fractions were combined and concentrated under reduced pressure, yielding 0.03 gram of the subject compound. The NMR spectrum was consistent with the proposed structure. The reaction was repeated.

Step D Synthesis of Compound 1

This compound was prepared in a manner analogous to that set forth in Step G of Example 1, using 0.17 gram (0.0007 mole) of 2-{[(6-chloro(3-pyridyl)methyl](2-chloroethylamino}ethanenitrile (prepared in Steps A and B of the present Example), 0.10 gram (0.00064 mole) of 2-ethylthio-3-nitropyrrole and 0.22 gram (0.0016 mole) of potassium carbonate in about 15 mL of DMF. The crude product was purified with column chromatography on silica gel. Elution was accomplished using 50% hexane in diethyl ether and 100% diethyl ether as eluants. The appropriate fractions were combined and concentrated under reduced pressure, yielding 0.10 gram of Compound I. The NMR spectrum was consistent with the proposed structure.

24

EXAMPLE 3

This example illustrates one protocol for the preparation of {2-[2-(dimethylamino)-3-nitropyrrolyl]ethyl}[(6-chloro(3-pyridyl))methyl][(4-chlorophenyl)methyl]amine (Compound 214)

Step A Synthesis of 2-{[(6-chloro(3-pyridyl)methyl][(4-chlorophenyl)methyl]amino}ethan-1-ol as an intermediate This compound was prepared in a manner analogous to that set forth in Step A of Example 1, using 5.0 grams (0.0268 mole) of 2-{[(6-chloro-3-pyridyl)methyl]amino}ethan-1-ol (prepared in Step A of Example 1), 3.8 grams (0.0268 mole) of 4-chlorobenzaldehyde, 8.5 grams (0.040 mole) of sodium triacetoxyborohydride and 6.5 grams (0.053 mole) of magnesium sulfate in 100 mL of 1,2-dichloroethane. The crude product was purified with column chromatography on silica gel. Elution was accomplished using 2% methanol in methylene chloride as an eluant. The appropriate fractions were combined and concentrated under reduced pressure, yielding 7.9 grams of the subject compound. The NMR spectrum was consistent with the proposed structure.

Step B Synthesis of [(6-chloro(3-pyridyl)methyl](2-chloroethyl)[(4-chlorophenyl)methyl]amine as an intermediate This compound was prepared in a manner analogous to that set forth in Step C of Example 1, using 6.0 grams (0.0193 mole) of 2-{[(6-chloro(3-pyridyl)methyl][(4-chlorophenyl)methyl]amino}ethan-1-ol, 2.4 grams (0.0203 mole) of thionyl chloride and four drops (catalyst) of pyridine in 75 mL of chloroform. The crude product was purified with column chromatography on silica gel. Elution was accomplished using 15% ethyl acetate in hexane then 30% ethyl acetate in hexane as eluants. The appropriate fractions were combined and concentrated under reduced pressure, yielding 5.7 grams of the subject compound. The NMR spectrum was consistent with the proposed structure.

Step C Synthesis of dimethyl(3-nitropyrrol-2-yl)amine as an intermediate

This compound was prepared in a manner analogous to that set forth in Step C of Example 2, using 0.65 gram (0.0045 mole) of 2-chloro-3-nitropyrrole (prepared in Steps D-F of Example 1) and 5.0 mL (excess) of dimethylamine. The microwave chemical reactor was maintained at 100° C. during a 45-minute period, after which time the reaction was considered to be complete. The crude product was purified with column chromatography on silica gel. Elution was accomplished using 25% hexane in diethyl ether, then 100% diethyl ether as eluants. The appropriate fractions were combined and concentrated under reduced pressure, yielding 0.2 gram of the subject compound. The NMR spectrum was consistent with the proposed structure.

Step D Synthesis of Compound 214

This compound was prepared in a manner analogous to that set forth in Step G of Example 1, using 0.47 gram (0.0014 mole) of [(6-chloro(3-pyridyl)methyl](2-chloroethyl)[(4-chlorophenyl)methyl]amine (prepared in Steps A and B of the present Example), 0.2 gram (0.0013 mole) of dimethyl(3-nitropyrrol-2-yl)amine and 0.45 gram (0.0032 mole) of potassium carbonate in 20 mL of DMF. The crude product was purified with column chromatography on silica gel. Elution was accomplished using 50% hexane in diethyl as an eluant. The appropriate fractions were combined and concentrated under reduced pressure, yielding 0.05 gram of Compound 214. The NMR spectrum was consistent with the proposed structure.

It is well known to one of ordinary skill in the art that compounds like the compounds of formula I of the present invention can contain optically active and racemic forms. It is also well known in the art that compounds like the compounds of formula I may contain stereoisomeric forms, tautomeric forms and/or exhibit polymorphism. It is to be understood that the present invention encompasses any racemic, optically active, polymorphic, tautomeric, or stereoisomeric form, or mixtures thereof. It should be noted that it is well known in the art how to prepare optically active forms, for example by resolution of a racemic mixture, or by synthesis from optically active intermediates.

The following table sets forth some additional examples of compounds of formula I useful in the present invention:

TABLE 1

Insecticidal N,N-Di(heteroarylalkyl)amine Derivatives

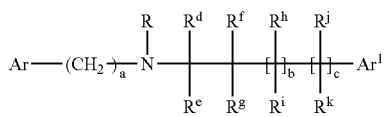

I wherein
Ar is selected from

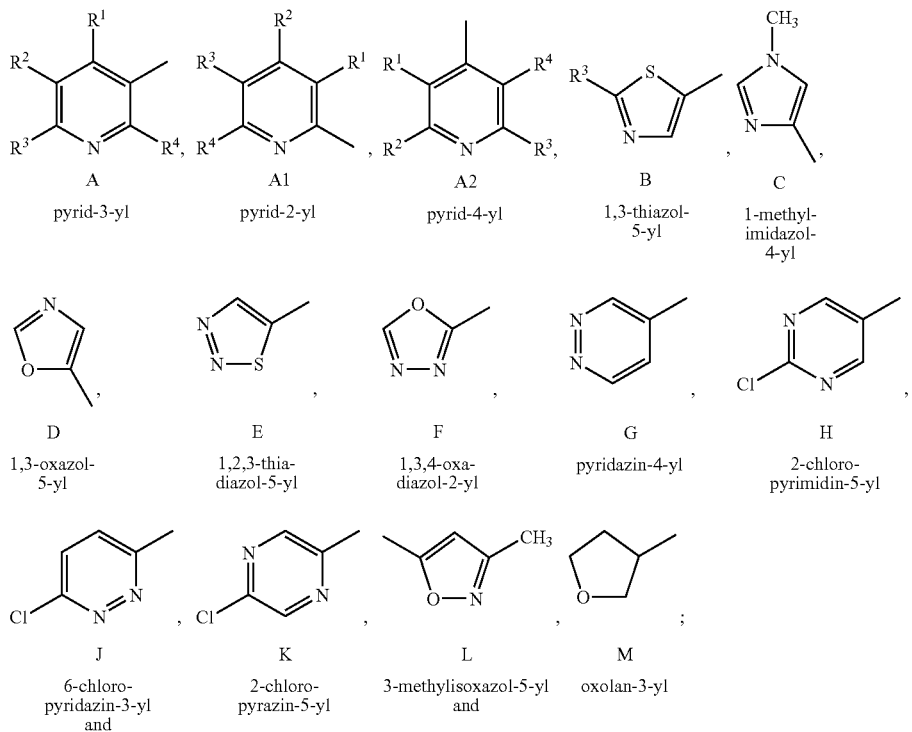

$Ar^1$ is selected from

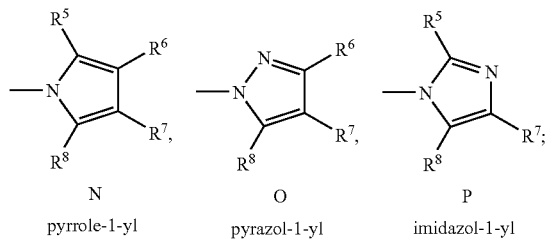

TABLE 1-continued where Ar is A; $Ar^1$ is N; a is 1; b and c are 0; $R^d$, $R^e$, $R^f$, $R^g$, $R^1$, $R^2$ $R^4$ are hydrogen, $R^3$ is chlorine,:

I-1

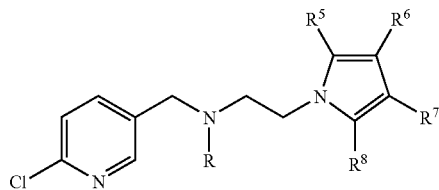

| Cmpd. No. | R | $R^5$ | $R^6$ | $R^7$ | $R^8$ |
|---|---|---|---|---|---|
| 1 | $CH_2CN$ | H | H | $NO_2$ | $SC_2H_5$ |
| 2 | $CH_2CN$ | H | H | $NO_2$ | $SCH_3$ |
| 3 | $CH_2CN$ | H | H | $NO_2$ | $NHCH_3$ |
| 4 | $CH_2CN$ | H | H | $NO_2$ | $N(CH_3)_2$ |
| 5 | $CH_2CN$ | H | H | $NO_2$ | $OCH_3$ |
| 6 | $CH_2CN$ | H | H | $NO_2$ | $OC_2H_5$ |
| 7 | $CH_2CN$ | H | H | $NO_2$ | $NO_2$ |
| 8 | $CH_2CN$ | H | H | $NO_2$ | Cl |
| 9 | $CH_2CN$ | H | H | $NO_2$ | F |
| 10 | $CH_2CN$ | H | H | $NO_2$ | Br |
| 11 | $CH_2CN$ | H | H | CN | $SC_2H_5$ |
| 12 | $CH_2CN$ | H | H | CN | $SCH_3$ |
| 13 | $CH_2CN$ | H | H | CN | $NHCH_3$ |
| 14 | $CH_2CN$ | H | H | CN | $N(CH_3)_2$ |
| 15 | $CH_2CN$ | H | H | CN | $OCH_3$ |
| 16 | $CH_2CN$ | H | H | CN | $OC_2H_5$ |
| 17 | $CH_2CN$ | H | H | CN | $NO_2$ |
| 18 | $CH_2CN$ | H | H | CN | Cl |
| 19 | $CH_2CN$ | H | H | CN | F |
| 20 | $CH_2CN$ | H | H | CN | Br |
| 21 | $CH_2CN$ | H | H | $CF_3$ | $SC_2H_5$ |
| 22 | $CH_2CN$ | H | H | $CF_3$ | $SCH_3$ |
| 23 | $CH_2CN$ | H | H | $CF_3$ | $NHCH_3$ |
| 24 | $CH_2CN$ | H | H | $CF_3$ | $N(CH_3)_2$ |
| 25 | $CH_2CN$ | H | H | $CF_3$ | $OCH_3$ |
| 26 | $CH_2CN$ | H | H | $CF_3$ | $OC_2H_5$ |
| 27 | $CH_2CN$ | H | H | $CF_3$ | $NO_2$ |
| 28 | $CH_2CN$ | H | H | $CF_3$ | Cl |
| 29 | $CH_2CN$ | H | H | $CF_3$ | F |
| 30 | $CH_2CN$ | H | H | $CF_3$ | Br |
| 31 | $CH_2C\equiv CH$ | H | H | $NO_2$ | $SC_2H_5$ |
| 32 | $CH_2C\equiv CH$ | H | H | $NO_2$ | $SCH_3$ |
| 33 | $CH_2C\equiv CH$ | H | H | $NO_2$ | $NHCH_3$ |
| 34 | $CH_2C\equiv CH$ | H | H | $NO_2$ | $N(CH_3)_2$ |
| 35 | $CH_2C\equiv CH$ | H | H | $NO_2$ | $OCH_3$ |
| 36 | $CH_2C\equiv CH$ | H | H | $NO_2$ | $OC_2H_5$ |
| 37 | $CH_2C\equiv CH$ | H | H | $NO_2$ | $NO_2$ |
| 38 | $CH_2C\equiv CH$ | H | H | $NO_2$ | Cl |
| 39 | $CH_2C\equiv CH$ | H | H | $NO_2$ | F |
| 40 | $CH_2C\equiv CH$ | H | H | $NO_2$ | Br |
| 41 | $CH_2C\equiv CH$ | H | H | CN | $SC_2H_5$ |
| 42 | $CH_2C\equiv CH$ | H | H | CN | $SCH_3$ |
| 43 | $CH_2C\equiv CH$ | H | H | CN | $NHCH_3$ |
| 44 | $CH_2C\equiv CH$ | H | H | CN | $N(CH_3)_2$ |
| 45 | $CH_2C\equiv CH$ | H | H | CN | $OCH_3$ |
| 46 | $CH_2C\equiv CH$ | H | H | CN | $OC_2H_5$ |
| 47 | $CH_2C\equiv CH$ | H | H | CN | $NO_2$ |
| 48 | $CH_2C\equiv CH$ | H | H | CN | Cl |
| 49 | $CH_2C\equiv CH$ | H | H | CN | F |
| 50 | $CH_2C\equiv CH$ | H | H | CN | Br |
| 51 | $CH_2C\equiv CH$ | H | H | $CF_3$ | $SC_2H_5$ |
| 52 | $CH_2C\equiv CH$ | H | H | $CF_3$ | $SCH_3$ |
| 53 | $CH_2C\equiv CH$ | H | H | $CF_3$ | $NHCH_3$ |
| 54 | $CH_2C\equiv CH$ | H | H | $CF_3$ | $N(CH_3)_2$ |
| 55 | $CH_2C\equiv CH$ | H | H | $CF_3$ | $OCH_3$ |
| 56 | $CH_2C\equiv CH$ | H | H | $CF_3$ | $OC_2H_5$ |
| 57 | $CH_2C\equiv CH$ | H | H | $CF_3$ | $NO_2$ |
| 58 | $CH_2C\equiv CH$ | H | H | $CF_3$ | Cl |
| 59 | $CH_2C\equiv CH$ | H | H | $CF_3$ | F |
| 60 | $CH_2C\equiv CH$ | H | H | $CF_3$ | Br |
| 61 | $CH_2C=CH_2$ | H | H | $NO_2$ | $SC_2H_5$ |
| 62 | $CH_2C=CH_2$ | H | H | $NO_2$ | $SCH_3$ |
| 63 | $CH_2C=CH_2$ | H | H | $NO_2$ | $NHCH_3$ |

TABLE 1-continued

|     |                                   |   |   |                 |                                   |
| --- | --------------------------------- | - | - | --------------- | --------------------------------- |
| 64  | CH$_2$C=CH$_2$                    | H | H | NO$_2$          | N(CH$_3$)$_2$                     |
| 65  | CH$_2$C=CH$_2$                    | H | H | NO$_2$          | OCH$_3$                           |
| 66  | CH$_2$C=CH$_2$                    | H | H | NO$_2$          | OC$_2$H$_5$                       |
| 67  | CH$_2$C=CH$_2$                    | H | H | NO$_2$          | NO$_2$                            |
| 68  | CH$_2$C=CH$_2$                    | H | H | NO$_2$          | Cl                                |
| 69  | CH$_2$C=CH$_2$                    | H | H | NO$_2$          | F                                 |
| 70  | CH$_2$C=CH$_2$                    | H | H | NO$_2$          | Br                                |
| 71  | CH$_2$C=CH$_2$                    | H | H | CN              | SC$_2$H$_5$                       |
| 72  | CH$_2$C=CH$_2$                    | H | H | CN              | SCH$_3$                           |
| 73  | CH$_2$C=CH$_2$                    | H | H | CN              | NHCH$_3$                          |
| 74  | CH$_2$C=CH$_2$                    | H | H | CN              | N(CH$_3$)$_2$                     |
| 75  | CH$_2$C=CH$_2$                    | H | H | CN              | OCH$_3$                           |
| 76  | CH$_2$C=CH$_2$                    | H | H | CN              | OC$_2$H$_5$                       |
| 77  | CH$_2$C=CH$_2$                    | H | H | CN              | NO$_2$                            |
| 78  | CH$_2$C=CH$_2$                    | H | H | CN              | Cl                                |
| 79  | CH$_2$C=CH$_2$                    | H | H | CN              | F                                 |
| 80  | CH$_2$C=CH$_2$                    | H | H | CN              | Br                                |
| 81  | CH$_2$C=CH$_2$                    | H | H | CF$_3$          | SC$_2$H$_5$                       |
| 82  | CH$_2$C=CH$_2$                    | H | H | CF$_3$          | SCH$_3$                           |
| 83  | CH$_2$C=CH$_2$                    | H | H | CF$_3$          | NHCH$_3$                          |
| 84  | CH$_2$C=CH$_2$                    | H | H | CF$_3$          | N(CH$_3$)$_2$                     |
| 85  | CH$_2$C=CH$_2$                    | H | H | CF$_3$          | OCH$_3$                           |
| 86  | CH$_2$C=CH$_2$                    | H | H | CF$_3$          | OC$_2$H$_5$                       |
| 87  | CH$_2$C=CH$_2$                    | H | H | CF$_3$          | NO$_2$                            |
| 88  | CH$_2$C=CH$_2$                    | H | H | CF$_3$          | Cl                                |
| 89  | CH$_2$C=CH$_2$                    | H | H | CF$_3$          | F                                 |
| 90  | CH$_2$C=CH$_2$                    | H | H | CF$_3$          | Br                                |
| 91  | CH$_2$C(CH$_3$)$_3$               | H | H | NO$_2$          | SC$_2$H$_5$                       |
| 92  | CH$_2$C(CH$_3$)$_3$               | H | H | NO$_2$          | SCH$_3$                           |
| 93  | CH$_2$C(CH$_3$)$_3$               | H | H | NO$_2$          | NHCH$_3$                          |
| 94  | CH$_2$C(CH$_3$)$_3$               | H | H | NO$_2$          | N(CH$_3$)$_2$                     |
| 95  | CH$_2$C(CH$_3$)$_3$               | H | H | NO$_2$          | OCH$_3$                           |
| 96  | CH$_2$C(CH$_3$)$_3$               | H | H | NO$_2$          | OC$_2$H$_5$                       |
| 97  | CH$_2$C(CH$_3$)$_3$               | H | H | NO$_2$          | NO$_2$                            |
| 98  | CH$_2$C(CH$_3$)$_3$               | H | H | NO$_2$          | Cl                                |
| 99  | CH$_2$C(CH$_3$)$_3$               | H | H | NO$_2$          | F                                 |
| 100 | CH$_2$C(CH$_3$)$_3$               | H | H | NO$_2$          | Br                                |
| 101 | CH$_2$C(CH$_3$)$_3$               | H | H | CN              | SC$_2$H$_5$                       |
| 102 | CH$_2$C(CH$_3$)$_3$               | H | H | CN              | SCH$_3$                           |
| 103 | CH$_2$C(CH$_3$)$_3$               | H | H | CN              | NHCH$_3$                          |
| 104 | CH$_2$C(CH$_3$)$_3$               | H | H | CN              | N(CH$_3$)$_2$                     |
| 105 | CH$_2$C(CH$_3$)$_3$               | H | H | CN              | OCH$_3$                           |
| 107 | CH$_2$C(CH$_3$)$_3$               | H | H | CN              | OC$_2$H$_5$                       |
| 106 | CH$_2$C(CH$_3$)$_3$               | H | H | CN              | NO$_2$                            |
| 108 | CH$_2$C(CH$_3$)$_3$               | H | H | CN              | Cl                                |
| 109 | CH$_2$C(CH$_3$)$_3$               | H | H | CN              | F                                 |
| 110 | CH$_2$C(CH$_3$)$_3$               | H | H | CN              | Br                                |
| 111 | CH$_2$C(CH$_3$)$_3$               | H | H | CF$_3$          | SC$_2$H$_5$                       |
| 112 | CH$_2$C(CH$_3$)$_3$               | H | H | CF$_3$          | SCH$_3$                           |
| 113 | CH$_2$C(CH$_3$)$_3$               | H | H | CF$_3$          | NHCH$_3$                          |
| 114 | CH$_2$C(CH$_3$)$_3$               | H | H | CF$_3$          | N(CH$_3$)$_2$                     |
| 115 | CH$_2$C(CH$_3$)$_3$               | H | H | CF$_3$          | OCH$_3$                           |
| 116 | CH$_2$C(CH$_3$)$_3$               | H | H | CF$_3$          | OC$_2$H$_5$                       |
| 117 | CH$_2$C(CH$_3$)$_3$               | H | H | CF$_3$          | NO$_2$                            |
| 118 | CH$_2$C(CH$_3$)$_3$               | H | H | CF$_3$          | Cl                                |
| 119 | CH$_2$C(CH$_3$)$_3$               | H | H | CF$_3$          | F                                 |
| 120 | CH$_2$C(CH$_3$)$_3$               | H | H | CF$_3$          | Br                                |
| 121 | CH$_2$CH(CH$_3$)$_2$              | H | H | NO$_2$          | SC$_2$H$_5$                       |
| 122 | CH$_2$CH(CH$_3$)$_2$              | H | H | NO$_2$          | SCH$_3$                           |
| 123 | CH$_2$CH(CH$_3$)$_2$              | H | H | NO$_2$          | NHCH$_3$                          |
| 124 | CH$_2$CH(CH$_3$)$_2$              | H | H | NO$_2$          | N(CH$_3$)$_2$                     |
| 125 | CH$_2$CH(CH$_3$)$_2$              | H | H | NO$_2$          | OCH$_3$                           |
| 126 | CH$_2$CH(CH$_3$)$_2$              | H | H | NO$_2$          | OC$_2$H$_5$                       |
| 127 | CH$_2$CH(CH$_3$)$_2$              | H | H | NO$_2$          | NO$_2$                            |
| 128 | CH$_2$CH(CH$_3$)$_2$              | H | H | NO$_2$          | Cl                                |
| 129 | CH$_2$CH(CH$_3$)$_2$              | H | H | NO$_2$          | F                                 |
| 130 | CH$_2$CH(CH$_3$)$_2$              | H | H | NO$_2$          | Br                                |
| 131 | CH$_2$CH(CH$_3$)$_2$              | H | H | CN              | SC$_2$H$_5$                       |
| 132 | CH$_2$CH(CH$_3$)$_2$              | H | H | CN              | SCH$_3$                           |
| 133 | CH$_2$CH(CH$_3$)$_2$              | H | H | CN              | NHCH$_3$                          |
| 134 | CH$_2$CH(CH$_3$)$_2$              | H | H | CN              | N(CH$_3$)$_2$                     |
| 135 | CH$_2$CH(CH$_3$)$_2$              | H | H | CN              | OCH$_3$                           |
| 136 | CH$_2$CH(CH$_3$)$_2$              | H | H | CN              | OC$_2$H$_5$                       |
| 137 | CH$_2$CH(CH$_3$)$_2$              | H | H | CN              | NO$_2$                            |
| 138 | CH$_2$CH(CH$_3$)$_2$              | H | H | CN              | Cl                                |
| 139 | CH$_2$CH(CH$_3$)$_2$              | H | H | CN              | F                                 |
| 140 | CH$_2$CH(CH$_3$)$_2$              | H | H | CN              | Br                                |
| 141 | CH$_2$CH(CH$_3$)$_2$              | H | H | CF$_3$          | SC$_2$H$_5$                       |
| 142 | CH$_2$CH(CH$_3$)$_2$              | H | H | CF$_3$          | SCH$_3$                           |
| 143 | CH$_2$CH(CH$_3$)$_2$              | H | H | CF$_3$          | NHCH$_3$                          |

TABLE 1-continued

| | | | | | |
|---|---|---|---|---|---|
| 144 | CH$_2$CH(CH$_3$)$_2$ | H | H | CF$_3$ | N(CH$_3$)$_2$ |
| 145 | CH$_2$CH(CH$_3$)$_2$ | H | H | CF$_3$ | OCH$_3$ |
| 146 | CH$_2$CH(CH$_3$)$_2$ | H | H | CF$_3$ | OC$_2$H$_5$ |
| 147 | CH$_2$CH(CH$_3$)$_2$ | H | H | CF$_3$ | NO$_2$ |
| 148 | CH$_2$CH(CH$_3$)$_2$ | H | H | CF$_3$ | Cl |
| 149 | CH$_2$CH(CH$_3$)$_2$ | H | H | CF$_3$ | F |
| 150 | CH$_2$CH(CH$_3$)$_2$ | H | H | CF$_3$ | Br |
| 151 | cyclohexylmethyl | H | H | NO$_2$ | SC$_2$H$_5$ |
| 152 | cyclohexylmethyl | H | H | NO$_2$ | SCH$_3$ |
| 153 | cyclohexylmethyl | H | H | NO$_2$ | NHCH$_3$ |
| 154 | cyclohexylmethyl | H | H | NO$_2$ | N(CH$_3$)$_2$ |
| 155 | cyclohexylmethyl | H | H | NO$_2$ | OCH$_3$ |
| 156 | cyclohexylmethyl | H | H | NO$_2$ | OC$_2$H$_5$ |
| 157 | cyclohexylmethyl | H | H | NO$_2$ | NO$_2$ |
| 158 | cyclohexylmethyl | H | H | NO$_2$ | Cl |
| 159 | cyclohexylmethyl | H | H | NO$_2$ | F |
| 160 | cyclohexylmethyl | H | H | NO$_2$ | Br |
| 161 | cyclohexylmethyl | H | H | CN | SC$_2$H$_5$ |
| 162 | cyclohexylmethyl | H | H | CN | SCH$_3$ |
| 163 | cyclohexylmethyl | H | H | CN | NHCH$_3$ |

TABLE 1-continued
| | | | | | |
|---|---|---|---|---|---|
| 164 | 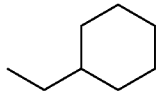 | H | H | CN | N(CH$_3$)$_2$ |
| 165 | 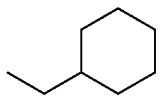 | H | H | CN | OCH$_3$ |
| 166 | 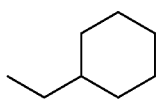 | H | H | CN | OC$_2$H$_5$ |
| 167 | 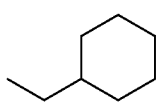 | H | H | CN | NO$_2$ |
| 168 | 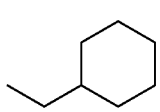 | H | H | CN | Cl |
| 169 | 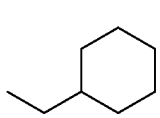 | H | H | CN | F |
| 170 | 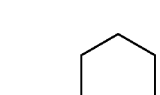 | H | H | CN | Br |
| 171 | 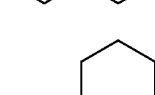 | H | H | CF$_3$ | SC$_2$H$_5$ |
| 172 | 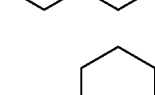 | H | H | CF$_3$ | SCH$_3$ |
| 173 | 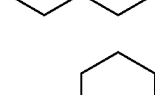 | H | H | CF$_3$ | NHCH$_3$ |
| 174 | 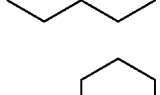 | H | H | CF$_3$ | N(CH$_3$)$_2$ |
| 175 | 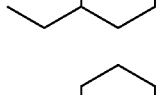 | H | H | CF$_3$ | OCH$_3$ |
| 176 | 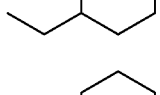 | H | H | CF$_3$ | OC$_2$H$_5$ |
| 177 | 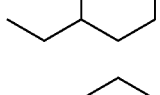 | H | H | CF$_3$ | NO$_2$ |

TABLE 1-continued

| | | | | | |
|---|---|---|---|---|---|
| 178 | ethylcyclohexyl | H | H | CF$_3$ | Cl |
| 179 | ethylcyclohexyl | H | H | CF$_3$ | F |
| 180 | ethylcyclohexyl | H | H | CF$_3$ | Br |
| 181 | 4-methoxybenzyl-ethyl | H | H | NO$_2$ | SC$_2$H$_5$ |
| 182 | 4-methoxybenzyl-ethyl | H | H | NO$_2$ | SCH$_3$ |
| 183 | 4-methoxybenzyl-ethyl | H | H | NO$_2$ | NHCH$_3$ |
| 184 | 4-methoxybenzyl-ethyl | H | H | NO$_2$ | N(CH$_3$)$_2$ |
| 185 | 4-methoxybenzyl-ethyl | H | H | NO$_2$ | OCH$_3$ |
| 186 | 4-methoxybenzyl-ethyl | H | H | NO$_2$ | OC$_2$H$_5$ |
| 187 | 4-methoxybenzyl-ethyl | H | H | NO$_2$ | NO$_2$ |
| 188 | 4-methoxybenzyl-ethyl | H | H | NO$_2$ | Cl |
| 189 | 4-methoxybenzyl-ethyl | H | H | NO$_2$ | F |
| 190 | 4-methoxybenzyl-ethyl | H | H | NO$_2$ | Br |
| 191 | 4-methoxybenzyl-ethyl | H | H | CN | SC$_2$H$_5$ |

TABLE 1-continued

| | | | | | |
|---|---|---|---|---|---|
| 192 | 4-OCH₃-C₆H₄-CH₂CH₂- | H | H | CN | SCH₃ |
| 193 | 4-OCH₃-C₆H₄-CH₂CH₂- | H | H | CN | NHCH₃ |
| 194 | 4-OCH₃-C₆H₄-CH₂CH₂- | H | H | CN | N(CH₃)₂ |
| 195 | 4-OCH₃-C₆H₄-CH₂CH₂- | H | H | CN | OCH₃ |
| 196 | 4-OCH₃-C₆H₄-CH₂CH₂- | H | H | CN | OC₂H₅ |
| 197 | 4-OCH₃-C₆H₄-CH₂CH₂- | H | H | CN | NO₂ |
| 198 | 4-OCH₃-C₆H₄-CH₂CH₂- | H | H | CN | Cl |
| 199 | 4-OCH₃-C₆H₄-CH₂CH₂- | H | H | CN | F |
| 200 | 4-OCH₃-C₆H₄-CH₂CH₂- | H | H | CN | Br |
| 201 | 4-OCH₃-C₆H₄-CH₂CH₂- | H | H | CF₃ | SC₂H₅ |
| 202 | 4-OCH₃-C₆H₄-CH₂CH₂- | H | H | CF₃ | SCH₃ |
| 203 | 4-OCH₃-C₆H₄-CH₂CH₂- | H | H | CF₃ | NHCH₃ |
| 204 | 4-OCH₃-C₆H₄-CH₂CH₂- | H | H | CF₃ | N(CH₃)₂ |
| 205 | 4-OCH₃-C₆H₄-CH₂CH₂- | H | H | CF₃ | OCH₃ |

TABLE 1-continued
| | | | | | |
|---|---|---|---|---|---|
| 206 | 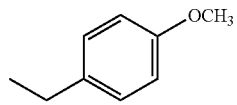 | H | H | CF$_3$ | OC$_2$H$_5$ |
| 207 | 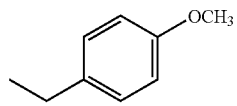 | H | H | CF$_3$ | NO$_2$ |
| 208 | 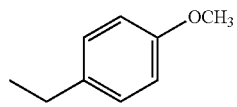 | H | H | CF$_3$ | Cl |
| 209 | 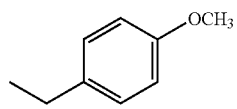 | H | H | CF$_3$ | F |
| 210 | 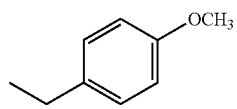 | H | H | CF$_3$ | Br |
| 211 | 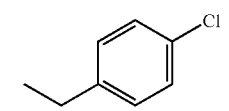 | H | H | NO$_2$ | SC$_2$H$_5$ |
| 212 | 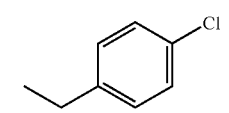 | H | H | NO$_2$ | SCH$_3$ |
| 213 | 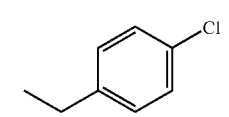 | H | H | NO$_2$ | NHCH$_3$ |
| 214 | 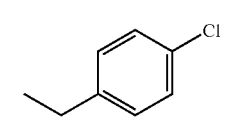 | H | H | NO$_2$ | N(CH$_3$)$_2$ |
| 215 | 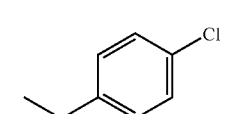 | H | H | NO$_2$ | OCH$_3$ |
| 216 | 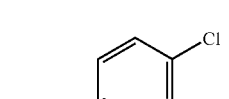 | H | H | NO$_2$ | OC$_2$H$_5$ |
| 217 | 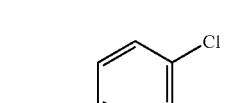 | H | H | NO$_2$ | NO$_2$ |
| 218 | 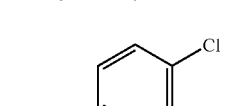 | H | H | NO$_2$ | Cl |

TABLE 1-continued
| | | | | | |
|---|---|---|---|---|---|
| 219 | 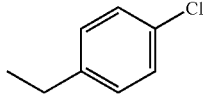 | H | H | NO₂ | F |
| 220 | 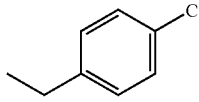 | H | H | NO₂ | Br |
| 221 | 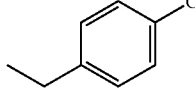 | H | H | CN | SC₂H₅ |
| 222 | 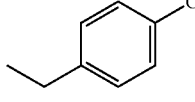 | H | H | CN | SCH₃ |
| 223 | 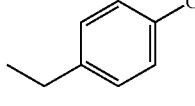 | H | H | CN | NHCH₃ |
| 224 | 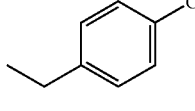 | H | H | CN | N(CH₃)₂ |
| 225 | 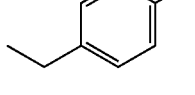 | H | H | CN | OCH₃ |
| 226 | 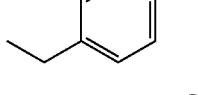 | H | H | CN | OC₂H₅ |
| 227 | 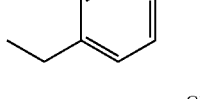 | H | H | CN | NO₂ |
| 228 | 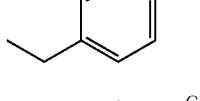 | H | H | CN | Cl |
| 229 | 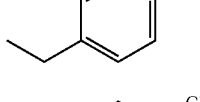 | H | H | CN | F |
| 230 | 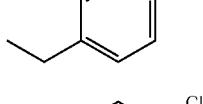 | H | H | CN | Br |
| 231 | 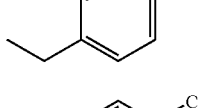 | H | H | CF₃ | SC₂H₅ |
| 232 | 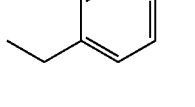 | H | H | CF₃ | SCH₃ |

TABLE 1-continued

| | | | | | |
|---|---|---|---|---|---|
| 233 | 4-Cl-C6H4-CH2CH2- | H | H | CF3 | NHCH3 |
| 234 | 4-Cl-C6H4-CH2CH2- | H | H | CF3 | N(CH3)2 |
| 235 | 4-Cl-C6H4-CH2CH2- | H | H | CF3 | OCH3 |
| 236 | 4-Cl-C6H4-CH2CH2- | H | H | CF3 | OC2H5 |
| 237 | 4-Cl-C6H4-CH2CH2- | H | H | CF3 | NO2 |
| 238 | 4-Cl-C6H4-CH2CH2- | H | H | CF3 | Cl |
| 239 | 4-Cl-C6H4-CH2CH2- | H | H | CF3 | F |
| 240 | 4-Cl-C6H4-CH2CH2- | H | H | CF3 | Br |
| 241 | C3H7 | CH3 | H | NO2 | SCH3 |
| 242 | 4-OCH3-C6H4-CH2CH2- | CH3 | H | NO2 | SCH3 |
| 243 | 4-OCH3-C6H4-CH2CH2- | CO2CH3 | H | NO2 | Cl |
| 244 | CH3 | H | H | NO2 | Cl |
| 245 | CH3 | H | H | NO2 | SC2H5 |
| 246 | CH2CN | CH3 | H | NO2 | Cl |
| 247 | CH2C≡CH | CH3 | H | NO2 | Cl |
| 248 | CH(CH3)2 | H | H | NO2 | Cl |
| 249 | cyclopropyl-CH2CH2- | H | H | NO2 | Cl |
| 250 | C2H4OC2H4OCH3 | H | H | NO2 | Cl |
| 251 | cyclopropyl-CH2CH2- | H | H | NO2 | SC2H5 |

TABLE 1-continued

| Cmpd. No. | | R⁶ | R⁷ | R⁸ |
|---|---|---|---|---|
| 252 | 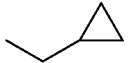 | H | H | NO₂ | N(CH₃)₂ |
| 253 | C₂H₄OC₂H₄OCH₃ | H | H | NO₂ | SC₂H₅ |
| 254 | CH(CH₃)₂ | H | H | NO₂ | SC₂H₅ |
| 255 | CH₂CH₂OCH₃ | H | H | NO₂ | Cl | where Ar is A; Ar¹ is O a is 1; b and c are 0; R$^d$, R$^e$, R$^f$, R$^g$, R¹, R² and R⁴ are hydrogen and R³ is chlorine,:

I-2

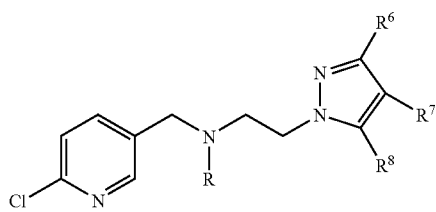

| Cmpd. No. | R | R⁶ | R⁷ | R⁸ |
|---|---|---|---|---|
| 256 | 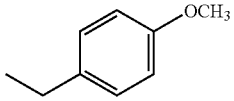 | Br | NO₂ | Br |
| 257 | CH₂CN | Br | NO₂ | Br |
| 258 | CH₂C≡CH | Br | NO₂ | Br |
| 259 | CH₂C(CH₃)₃ | Br | NO₂ | Br |
| 260 | CH₃ | Br | NO₂ | Br |
| 261 | CH₂CN | H | NO₂ | SC₂H₅ |
| 262 | CH₂CN | H | NO₂ | N(CH₃)₂ |
| 263 | CH₂CN | H | NO₂ | OCH₃ |
| 264 | CH₂CN | H | NO₂ | Cl |
| 265 | CH₂C≡CH | H | NO₂ | SC₂H₅ |
| 266 | CH₂C≡CH | H | NO₂ | N(CH₃)₂ |
| 267 | CH₂C≡CH | H | NO₂ | OCH₃ |
| 268 | CH₂C≡CH | H | NO₂ | Cl |
| 269 | CH₂CH(CH₃)₂ | H | NO₂ | SC₂H₅ |
| 270 | CH₂CH(CH₃)₂ | H | NO₂ | N(CH₃)₂ |
| 271 | CH₂CH(CH₃)₂ | H | NO₂ | OCH₃ |
| 272 | CH₂CH(CH₃)₂ | H | NO₂ | Cl |
| 273 | 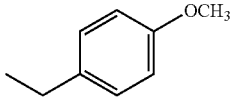 | H | NO₂ | SC₂H₅ |
| 274 | 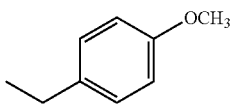 | H | NO₂ | N(CH₃)₂ |
| 275 | 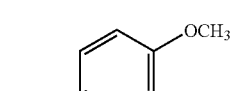 | H | NO₂ | OCH₃ |

TABLE 1-continued

| 276 |  | H | NO$_2$ | Cl | where Ar is A; Ar$^1$ is P; a is 1; b and c are 0; R$^d$, R$^e$, R$^f$, R$^1$, R$^2$ and R$^4$ are hydrogen and R$^3$ is chlorine

I-3

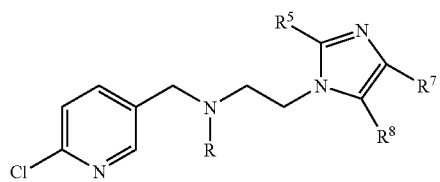

| Cmpd. No. | R | R$^5$ | R$^7$ | R$^8$ |
|---|---|---|---|---|
| 277 | 4-Cl-phenyl-CH$_2$CH$_2$- | H | NO$_2$ | NO$_2$ |
| 278 | 4-Cl-phenyl-CH$_2$CH$_2$- | H | Cl | NO$_2$ |
| 279 | 4-Cl-phenyl-CH$_2$CH$_2$- | H | NO$_2$ | Cl |
| 280 | CH$_3$ | H | Cl | NO$_2$ |
| 281 | CH$_3$ | H | NO$_2$ | Cl |
| 282 | CH$_2$C≡CH | H | NO$_2$ | NO$_2$ |
| 283 | CH$_2$C≡CH | H | Cl | NO$_2$ |
| 284 | CH$_2$CN | H | NO$_2$ | NO$_2$ |
| 285 | CH$_2$CN | H | Cl | NO$_2$ |
| 286 | CH$_2$CN | H | NO$_2$ | SC$_2$H$_5$ |
| 287 | CH$_2$CN | H | NO$_2$ | N(CH$_3$)$_2$ |
| 288 | CH$_2$CN | H | NO$_2$ | OCH$_3$ |
| 289 | CH$_2$CN | H | NO$_2$ | Cl |
| 290 | CH$_2$C≡CH | H | NO$_2$ | SC$_2$H$_5$ |
| 291 | CH$_2$C≡CH | H | NO$_2$ | N(CH$_3$)$_2$ |
| 292 | CH$_2$C≡CH | H | NO$_2$ | OCH$_3$ |
| 293 | CH$_2$C≡CH | H | NO$_2$ | Cl |
| 294 | CH$_2$CH(CH$_3$)$_2$ | H | NO$_2$ | SC$_2$H$_5$ |
| 295 | CH$_2$CH(CH$_3$)$_2$ | H | NO$_2$ | N(CH$_3$)$_2$ |
| 296 | CH$_2$CH(CH$_3$)$_2$ | H | NO$_2$ | OCH$_3$ |
| 297 | CH$_2$CH(CH$_3$)$_2$ | H | NO$_2$ | Cl |
| 298 | 4-OCH$_3$-phenyl-CH$_2$CH$_2$- | H | NO$_2$ | SC$_2$H$_5$ |
| 299 | 4-OCH$_3$-phenyl-CH$_2$CH$_2$- | H | NO$_2$ | N(CH$_3$)$_2$ |
| 300 | 4-OCH$_3$-phenyl-CH$_2$CH$_2$- | H | NO$_2$ | OCH$_3$ |

TABLE 1-continued

| 301 | | H | NO$_2$ | Cl | where Ar is N; a is 1; b and c are 0; R$^d$, R$^e$, R$^f$ and R$^g$ are hydrogen:

I-4

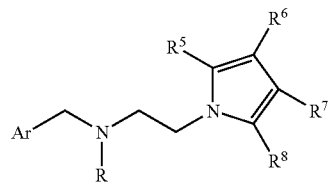

| Cmpd. No. | Ar | R | R$^5$ | R$^6$ | R$^7$ | R$^8$ |
| --- | --- | --- | --- | --- | --- | --- |
| 302 | M | CH$_2$C(CH$_3$)$_3$ | H | H | NO$_2$ | Cl |
| 303 | M | CH$_2$C(CH$_3$)$_3$ | H | H | NO$_2$ | SC$_2$H$_5$ |
| 304 | B* | C$_2$H$_4$OCH$_3$ | H | H | NO$_2$ | Cl |
| 305 | B* | | H | H | NO$_2$ | Cl |
| 306 | M | CH$_2$CN | H | H | NO$_2$ | SC$_2$H$_5$ |
| 307 | M | CH$_2$CN | H | H | NO$_2$ | N(CH$_3$)$_2$ |
| 308 | M | CH$_2$CN | H | H | NO$_2$ | OCH$_3$ |
| 309 | M | CH$_2$CN | H | H | NO$_2$ | Cl |
| 310 | M | CH$_2$C≡CH | H | H | NO$_2$ | SC$_2$H$_5$ |
| 311 | M | CH$_2$C≡CH | H | H | NO$_2$ | N(CH$_3$)$_2$ |
| 312 | M | CH$_2$C≡CH | H | H | NO$_2$ | OCH$_3$ |
| 313 | M | CH$_2$C≡CH | H | H | NO$_2$ | Cl |
| 314 | M | CH$_2$CH(CH$_3$)2 | H | H | NO$_2$ | SC$_2$H$_5$ |
| 315 | M | CH$_2$CH(CH$_3$)2 | H | H | NO$_2$ | N(CH$_3$)$_2$ |
| 316 | M | CH$_2$CH(CH$_3$)2 | H | H | NO$_2$ | OCH$_3$ |
| 317 | M | CH$_2$CH(CH$_3$)2 | H | H | NO$_2$ | Cl |
| 318 | M | | H | H | NO$_2$ | SC$_2$H$_5$ |
| 319 | M | | H | H | NO$_2$ | N(CH$_3$)$_2$ |
| 320 | M | | H | H | NO$_2$ | OCH$_3$ |
| 321 | M | | H | H | NO$_2$ | Cl |
| 322 | B* | CH$_2$CN | H | H | NO$_2$ | SC$_2$H$_5$ |
| 323 | B* | CH$_2$CN | H | H | NO$_2$ | N(CH$_3$)$_2$ |
| 324 | B* | CH$_2$CN | H | H | NO$_2$ | OCH$_3$ |
| 325 | B* | CH$_2$CN | H | H | NO$_2$ | Cl |
| 326 | B* | CH$_2$C≡CH | H | H | NO$_2$ | SC$_2$H$_5$ |
| 327 | B* | CH$_2$C≡CH | H | H | NO$_2$ | N(CH$_3$)$_2$ |
| 328 | B* | CH$_2$C≡CH | H | H | NO$_2$ | OCH$_3$ |
| 329 | B* | CH$_2$C≡CH | H | H | NO$_2$ | Cl |
| 330 | B* | CH$_2$CH(CH$_3$)$_2$ | H | H | NO$_2$ | SC$_2$H$_5$ |
| 331 | B* | CH$_2$CH(CH$_3$)$_2$ | H | H | NO$_2$ | N(CH$_3$)$_2$ |
| 332 | B* | CH$_2$CH(CH$_3$)$_2$ | H | H | NO$_2$ | OCH$_3$ |
| 333 | B* | CH$_2$CH(CH$_3$)$_2$ | H | H | NO$_2$ | Cl |

TABLE 1-continued

| 334 | B* | 4-ethyl-methoxyphenyl | H | H | NO$_2$ | SC$_2$H$_5$ |
| 335 | B* | 4-ethyl-methoxyphenyl | H | H | NO$_2$ | N(CH$_3$)$_2$ |
| 336 | B* | 4-ethyl-methoxyphenyl | H | H | NO$_2$ | OCH$_3$ |
| 337 | B* | 4-ethyl-methoxyphenyl | H | H | NO$_2$ | Cl |

*R$^3$ is Cl
where Ar$^1$ is O; a is 1; b and c are 0; R$^d$, R$^e$, R$^f$ and R$^g$ are hydrogen:

I-5

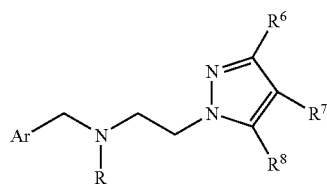

| Cmpd. No. | Ar | R | R$^6$ | R$^7$ | R$^8$ |
|---|---|---|---|---|---|
| 338 | M | CH$_2$CN | H | NO$_2$ | SC$_2$H$_5$ |
| 339 | M | CH$_2$CN | H | NO$_2$ | N(CH$_3$)$_2$ |
| 340 | M | CH$_2$CN | H | NO$_2$ | OCH$_3$ |
| 341 | M | CH$_2$CN | H | NO$_2$ | Cl |
| 342 | M | CH$_2$C≡CH | H | NO$_2$ | SC$_2$H$_5$ |
| 343 | M | CH$_2$C≡CH | H | NO$_2$ | N(CH$_3$)$_2$ |
| 344 | M | CH$_2$C≡CH | H | NO$_2$ | OCH$_3$ |
| 345 | M | CH$_2$C≡CH | H | NO$_2$ | Cl |
| 346 | M | CH$_2$CH(CH$_3$)$_2$ | H | NO$_2$ | SC$_2$H$_5$ |
| 347 | M | CH$_2$CH(CH$_3$)$_2$ | H | NO$_2$ | N(CH$_3$)$_2$ |
| 348 | M | CH$_2$CH(CH$_3$)$_2$ | H | NO$_2$ | OCH$_3$ |
| 349 | M | CH$_2$CH(CH$_3$)$_2$ | H | NO$_2$ | Cl |
| 350 | M | 4-ethyl-methoxyphenyl | H | NO$_2$ | SC$_2$H$_5$ |
| 351 | M | 4-ethyl-methoxyphenyl | H | NO$_2$ | N(CH$_3$)$_2$ |
| 352 | M | 4-ethyl-methoxyphenyl | H | NO$_2$ | OCH$_3$ |
| 353 | M | 4-ethyl-methoxyphenyl | H | NO$_2$ | Cl |
| 354 | B* | CH$_2$CN | H | NO$_2$ | SC$_2$H$_5$ |
| 355 | B* | CH$_2$CN | H | NO$_2$ | N(CH$_3$)$_2$ |
| 356 | B* | CH$_2$CN | H | NO$_2$ | OCH$_3$ |
| 357 | B* | CH$_2$CN | H | NO$_2$ | Cl |

TABLE 1-continued

| Cmpd. No. | Ar¹ | R | R⁵ | R⁷ | R⁸ |
|---|---|---|---|---|---|
| 358 | B* | CH₂C≡CH | H | NO₂ | SC₂H₅ |
| 359 | B* | CH₂C≡CH | H | NO₂ | N(CH₃)₂ |
| 360 | B* | CH₂C≡CH | H | NO₂ | OCH₃ |
| 361 | B* | CH₂C≡CH | H | NO₂ | Cl |
| 362 | B* | CH₂CH(CH₃)₂ | H | NO₂ | SC₂H₅ |
| 363 | B* | CH₂CH(CH₃)₂ | H | NO₂ | N(CH₃)₂ |
| 364 | B* | CH₂CH(CH₃)₂ | H | NO₂ | OCH₃ |
| 365 | B* | CH₂CH(CH₃)₂ | H | NO₂ | Cl |
| 366 | B* | 4-OCH₃-benzyl-ethyl | H | NO₂ | SC₂H₅ |
| 367 | B* | 4-OCH₃-benzyl-ethyl | H | NO₂ | N(CH₃)₂ |
| 368 | B* | 4-OCH₃-benzyl-ethyl | H | NO₂ | OCH₃ |
| 369 | B* | 4-OCH₃-benzyl-ethyl | H | NO₂ | Cl |

*R³ is Cl where Ar¹ is P; a is 1; b and c are 0; $R^d$, $R^e$, $R^f$ and $R^g$ are hydrogen:

I-6

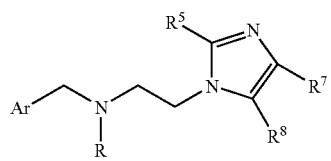

| Cmpd. No. | Ar | R | R⁵ | R⁷ | R⁸ |
|---|---|---|---|---|---|
| 370 | M | CH₂CN | H | NO₂ | SC₂H₅ |
| 371 | M | CH₂CN | H | NO₂ | N(CH₃)₂ |
| 372 | M | CH₂CN | H | NO₂ | OCH₃ |
| 373 | M | CH₂CN | H | NO₂ | Cl |
| 374 | M | CH₂C≡CH | H | NO₂ | SC₂H₅ |
| 375 | M | CH₂C≡CH | H | NO₂ | N(CH₃)₂ |
| 376 | M | CH₂C≡CH | H | NO₂ | OCH₃ |
| 377 | M | CH₂C≡CH | H | NO₂ | Cl |
| 378 | M | CH₂CH(CH₃)₂ | H | NO₂ | SC₂H₅ |
| 379 | M | CH₂CH(CH₃)₂ | H | NO₂ | N(CH₃)₂ |
| 380 | M | CH₂CH(CH₃)₂ | H | NO₂ | OCH₃ |
| 381 | M | CH₂CH(CH₃)₂ | H | NO₂ | Cl |
| 382 | M | 4-OCH₃-benzyl-ethyl | H | NO₂ | SC₂H₅ |
| 383 | M | 4-OCH₃-benzyl-ethyl | H | NO₂ | N(CH₃)₂ |
| 384 | M | 4-OCH₃-benzyl-ethyl | H | NO₂ | OCH₃ |

TABLE 1-continued

| 385 | M | [4-ethyl-phenyl with OCH₃] | H | NO₂ | Cl |

| 386 | B* | CH₂CN | H | NO₂ | SC₂H₅ |
| 387 | B* | CH₂CN | H | NO₂ | N(CH₃)₂ |
| 388 | B* | CH₂CN | H | NO₂ | OCH₃ |
| 389 | B* | CH₂CN | H | NO₂ | Cl |
| 390 | B* | CH₂C≡CH | H | NO₂ | SC₂H₅ |
| 391 | B* | CH₂C≡CH | H | NO₂ | N(CH₃)₂ |
| 392 | B* | CH₂C≡CH | H | NO₂ | OCH₃ |
| 393 | B* | CH₂C≡CH | H | NO₂ | Cl |
| 394 | B* | CH₂CH(CH₃)₂ | H | NO₂ | SC₂H₅ |
| 395 | B* | CH₂CH(CH₃)₂ | H | NO₂ | N(CH₃)₂ |
| 396 | B* | CH₂CH(CH₃)₂ | H | NO₂ | OCH₃ |
| 397 | B* | CH₂CH(CH₃)₂ | H | NO₂ | Cl |
| 398 | B* | [4-ethyl-phenyl with OCH₃] | H | NO₂ | SC₂H₅ |
| 399 | B* | [4-ethyl-phenyl with OCH₃] | H | NO₂ | N(CH₃)₂ |
| 400 | B* | [4-ethyl-phenyl with OCH₃] | H | NO₂ | OCH₃ |
| 401 | B* | [4-ethyl-phenyl with OCH₃] | H | NO₂ | Cl |

*$R^3$ is Cl
where $Ar^1$ is N; a and b are 1; c is 0; $R^d$, $R^e$, $R^f$, $R^g$, $R^i$ are hydrogen:

I-7

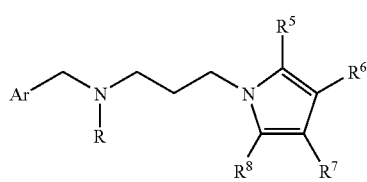

| Cmpd. No. | Ar | R | $R^5$ | $R^6$ | $R^7$ | $R^8$ |
|---|---|---|---|---|---|---|
| 402 | A** | CH₂CN | H | H | NO₂ | SC₂H₅ |
| 403 | A** | CH₂CN | H | H | NO₂ | N(CH₃)₂ |
| 404 | A** | CH₂CN | H | H | NO₂ | OCH₃ |
| 405 | A** | CH₂CN | H | H | NO₂ | Cl |
| 406 | A** | CH₂C≡CH | H | H | NO₂ | SC₂H₅ |
| 407 | A** | CH₂C≡CH | H | H | NO₂ | N(CH₃)₂ |
| 408 | A** | CH₂C≡CH | H | H | NO₂ | OCH₃ |
| 409 | A** | CH₂C≡CH | H | H | NO₂ | Cl |
| 410 | A** | CH₂CH(CH₃)₂ | H | H | NO₂ | SC₂H₅ |
| 411 | A** | CH₂CH(CH₃)₂ | H | H | NO₂ | N(CH₃)₂ |
| 412 | A** | CH₂CH(CH₃)₂ | H | H | NO₂ | OCH₃ |
| 413 | A** | CH₂CH(CH₃)₂ | H | H | NO₂ | Cl |
| 414 | A** | [4-ethyl-phenyl with OCH₃] | H | H | NO₂ | SC₂H₅ |

TABLE 1-continued

| | | | | | | |
|---|---|---|---|---|---|---|
| 415 | A** | 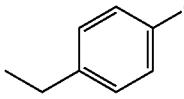 | H | H | NO$_2$ | N(CH$_3$)$_2$ |
| 416 | A** | 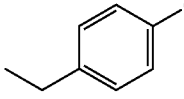 | H | H | NO$_2$ | OCH$_3$ |
| 417 | A** | 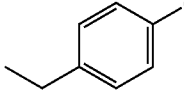 | H | H | NO$_2$ | Cl |
| 418 | A** | 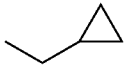 | H | H | NO$_2$ | Cl |
| 419 | A** | CH$_2$CH$_2$OCH$_3$ | H | H | NO$_2$ | Cl |
| 420 | M | CH$_2$CN | H | H | NO$_2$ | SC$_2$H$_5$ |
| 421 | M | CH$_2$CN | H | H | NO$_2$ | N(CH$_3$)$_2$ |
| 422 | M | CH$_2$CN | H | H | NO$_2$ | OCH$_3$ |
| 423 | M | CH$_2$CN | H | H | NO$_2$ | Cl |
| 424 | M | CH$_2$C≡CH | H | H | NO$_2$ | SC$_2$H$_5$ |
| 425 | M | CH$_2$C≡CH | H | H | NO$_2$ | N(CH$_3$)$_2$ |
| 426 | M | CH$_2$C≡CH | H | H | NO$_2$ | OCH$_3$ |
| 427 | M | CH$_2$C≡CH | H | H | NO$_2$ | Cl |
| 428 | M | CH$_2$CH(CH$_3$)$_2$ | H | H | NO$_2$ | SC$_2$H$_5$ |
| 429 | M | CH$_2$CH(CH$_3$)$_2$ | H | H | NO$_2$ | N(CH$_3$)$_2$ |
| 430 | M | CH$_2$CH(CH$_3$)$_2$ | H | H | NO$_2$ | OCH$_3$ |
| 431 | M | CH$_2$CH(CH$_3$)$_2$ | H | H | NO$_2$ | Cl |
| 432 | M | 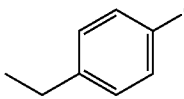 | H | H | NO$_2$ | SC$_2$H$_5$ |
| 433 | M | 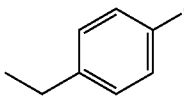 | H | H | NO$_2$ | N(CH$_3$)$_2$ |
| 434 | M | 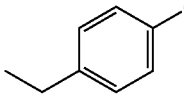 | H | H | NO$_2$ | OCH$_3$ |
| 435 | M | 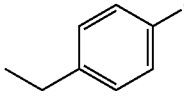 | H | H | NO$_2$ | Cl |
| 436 | B* | CH$_2$CN | H | H | NO$_2$ | SC$_2$H$_5$ |
| 437 | B* | CH$_2$CN | H | H | NO$_2$ | N(CH$_3$)$_2$ |
| 438 | B* | CH$_2$CN | H | H | NO$_2$ | OCH$_3$ |
| 439 | B* | CH$_2$CN | H | H | NO$_2$ | Cl |
| 440 | B* | CH$_2$C≡CH | H | H | NO$_2$ | SC$_2$H$_5$ |
| 441 | B* | CH$_2$C≡CH | H | H | NO$_2$ | N(CH$_3$)$_2$ |
| 442 | B* | CH$_2$C≡CH | H | H | NO$_2$ | OCH$_3$ |
| 443 | B* | CH$_2$C≡CH | H | H | NO$_2$ | Cl |
| 444 | B* | CH$_2$CH(CH$_3$)$_2$ | H | H | NO$_2$ | SC$_2$H$_5$ |
| 445 | B* | CH$_2$CH(CH$_3$)$_2$ | H | H | NO$_2$ | N(CH$_3$)$_2$ |
| 446 | B* | CH$_2$CH(CH$_3$)$_2$ | H | H | NO$_2$ | OCH$_3$ |
| 447 | B* | CH$_2$CH(CH$_3$)$_2$ | H | H | NO$_2$ | Cl |
| 448 | B* | 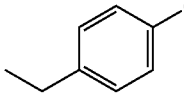 | H | H | NO$_2$ | SC$_2$H$_5$ |

TABLE 1-continued

| Cmpd. No. | Ar | R | R⁶ | R⁷ | R⁸ |
|---|---|---|---|---|---|
| 449 | B* | 4-ethyl-methoxyphenyl-CH₂ | H | H | NO₂ | N(CH₃)₂ |
| 450 | B* | 4-ethyl-methoxyphenyl-CH₂ | H | H | NO₂ | OCH₃ |
| 451 | B* | 4-ethyl-methoxyphenyl-CH₂ | H | H | NO₂ | Cl |

*R³ is Cl
**R¹, R² and R⁴ are hydrogen and R³ is chlorine
where Ar¹ is O; a and b are 1; c is 0; $R^d$, $R^e$, $R^f$, $R^g$, $R^h$ and $R^i$ are hydrogen:

I-8

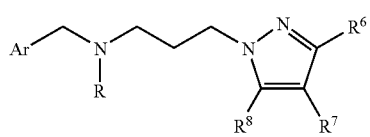

| Cmpd. No. | Ar | R | R⁶ | R⁷ | R⁸ |
|---|---|---|---|---|---|
| 452 | A** | CH₂CN | H | NO₂ | SC₂H₅ |
| 453 | A** | CH₂CN | H | NO₂ | N(CH₃)₂ |
| 454 | A** | CH₂CN | H | NO₂ | OCH₃ |
| 455 | A** | CH₂CN | H | NO₂ | Cl |
| 456 | A** | CH₂C≡CH | H | NO₂ | SC₂H₅ |
| 457 | A** | CH₂C≡CH | H | NO₂ | N(CH₃)₂ |
| 458 | A** | CH₂C≡CH | H | NO₂ | OCH₃ |
| 459 | A** | CH₂C≡CH | H | NO₂ | Cl |
| 460 | A** | CH₂CH(CH₃)₂ | H | NO₂ | SC₂H₅ |
| 461 | A** | CH₂CH(CH₃)₂ | H | NO₂ | N(CH₃)₂ |
| 462 | A** | CH₂CH(CH₃)₂ | H | NO₂ | OCH₃ |
| 463 | A** | CH₂CH(CH₃)₂ | H | NO₂ | Cl |
| 464 | A** | 4-ethyl-methoxyphenyl-CH₂ | H | NO₂ | SC₂H₅ |
| 465 | A** | 4-ethyl-methoxyphenyl-CH₂ | H | NO₂ | N(CH₃)₂ |
| 466 | A** | 4-ethyl-methoxyphenyl-CH₂ | H | NO₂ | OCH₃ |
| 467 | A** | 4-ethyl-methoxyphenyl-CH₂ | H | NO₂ | Cl |
| 468 | M | CH₂CN | H | NO₂ | SC₂H₅ |
| 469 | M | CH₂CN | H | NO₂ | N(CH₃)₂ |
| 470 | M | CH₂CN | H | NO₂ | OCH₃ |
| 471 | M | CH₂CN | H | NO₂ | Cl |
| 472 | M | CH₂C≡CH | H | NO₂ | SC₂H₅ |
| 473 | M | CH₂C≡CH | H | NO₂ | N(CH₃)₂ |
| 474 | M | CH₂C≡CH | H | NO₂ | OCH₃ |
| 475 | M | CH₂C≡CH | H | NO₂ | Cl |
| 476 | M | CH₂CH(CH₃)₂ | H | NO₂ | SC₂H₅ |
| 477 | M | CH₂CH(CH₃)₂ | H | NO₂ | N(CH₃)₂ |
| 478 | M | CH₂CH(CH₃)₂ | H | NO₂ | OCH₃ |
| 479 | M | CH₂CH(CH₃)₂ | H | NO₂ | Cl |

TABLE 1-continued

| Cmpd No. | | | | | |
|---|---|---|---|---|---|
| 480 | M | 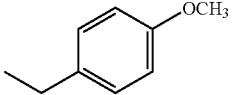 4-ethyl-methoxybenzene | H | $NO_2$ | $SC_2H_5$ |
| 481 | M | 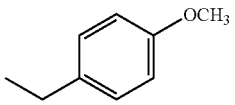 4-ethyl-methoxybenzene | H | $NO_2$ | $N(CH_3)_2$ |
| 482 | M | 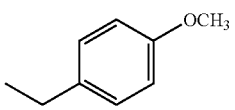 4-ethyl-methoxybenzene | H | $NO_2$ | $OCH_3$ |
| 483 | M | 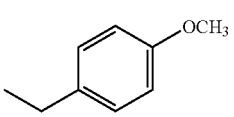 4-ethyl-methoxybenzene | H | $NO_2$ | Cl |
| 484 | B* | $CH_2CN$ | H | $NO_2$ | $SC_2H_5$ |
| 485 | B* | $CH_2CN$ | H | $NO_2$ | $N(CH_3)_2$ |
| 486 | B* | $CH_2CN$ | H | $NO_2$ | $OCH_3$ |
| 487 | B* | $CH_2CN$ | H | $NO_2$ | Cl |
| 488 | B* | $CH_2C{\equiv}CH$ | H | $NO_2$ | $SC_2H_5$ |
| 489 | B* | $CH_2C{\equiv}CH$ | H | $NO_2$ | $N(CH_3)_2$ |
| 490 | B* | $CH_2C{\equiv}CH$ | H | $NO_2$ | $OCH_3$ |
| 491 | B* | $CH_2C{\equiv}CH$ | H | $NO_2$ | Cl |
| 492 | B* | $CH_2CH(CH_3)_2$ | H | $NO_2$ | $SC_2H_5$ |
| 493 | B* | $CH_2CH(CH_3)_2$ | H | $NO_2$ | $N(CH_3)_2$ |
| 494 | B* | $CH_2CH(CH_3)_2$ | H | $NO_2$ | $OCH_3$ |
| 495 | B* | $CH_2CH(CH_3)_2$ | H | $NO_2$ | Cl |
| 496 | B* | 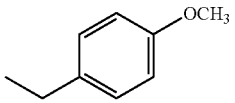 | H | $NO_2$ | $SC_2H_5$ |
| 497 | B* | 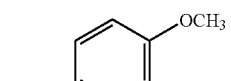 | H | $NO_2$ | $N(CH_3)_2$ |
| 498 | B* | 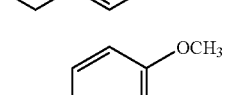 | H | $NO_2$ | $OCH_3$ |
| 499 | B* | 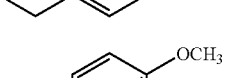 | H | $NO_2$ | Cl |

*$R^3$ is Cl
**$R^1$, $R^2$ and $R^4$ are hydrogen and $R^3$ is chlorine
where $Ar^1$ is P; a and b are 1; c is 0; $R^d$, $R^e$, $R^f$, $R^g$, $R^h$ and $R^i$ are hydrogen:

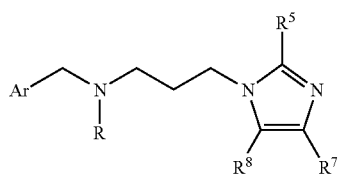

I-9

| Cmpd. No. | Ar | R | $R^5$ | $R^7$ | $R^8$ |
|---|---|---|---|---|---|
| 500 | A** | $CH_2CN$ | H | $NO_2$ | $SC_2H_5$ |
| 501 | A** | $CH_2CN$ | H | $NO_2$ | $N(CH_3)_2$ |
| 502 | A** | $CH_2CN$ | H | $NO_2$ | $OCH_3$ |

TABLE 1-continued

| | | | | | |
|---|---|---|---|---|---|
| 503 | A** | CH₂CN | H | NO₂ | Cl |
| 504 | A** | CH₂C≡CH | H | NO₂ | SC₂H₅ |
| 505 | A** | CH₂C≡CH | H | NO₂ | N(CH₃)₂ |
| 506 | A** | CH₂C≡CH | H | NO₂ | OCH₃ |
| 507 | A** | CH₂C≡CH | H | NO₂ | Cl |
| 508 | A** | CH₂CH(CH₃)₂ | H | NO₂ | SC₂H₅ |
| 509 | A** | CH₂CH(CH₃)₂ | H | NO₂ | N(CH₃)₂ |
| 510 | A** | CH₂CH(CH₃)₂ | H | NO₂ | OCH₃ |
| 511 | A** | CH₂CH(CH₃)₂ | H | NO₂ | Cl |
| 512 | A** | 4-OCH₃-C₆H₄-CH₂CH₂- | H | NO₂ | SC₂H₅ |
| 513 | A** | 4-OCH₃-C₆H₄-CH₂CH₂- | H | NO₂ | N(CH₃)₂ |
| 514 | A** | 4-OCH₃-C₆H₄-CH₂CH₂- | H | NO₂ | OCH₃ |
| 515 | A** | 4-OCH₃-C₆H₄-CH₂CH₂- | H | NO₂ | Cl |
| 516 | M | CH₂CN | H | NO₂ | SC₂H₅ |
| 517 | M | CH₂CN | H | NO₂ | N(CH₃)₂ |
| 518 | M | CH₂CN | H | NO₂ | OCH₃ |
| 519 | M | CH₂CN | H | NO₂ | Cl |
| 520 | M | CH₂C≡CH | H | NO₂ | SC₂H₅ |
| 521 | M | CH₂C≡CH | H | NO₂ | N(CH₃)₂ |
| 522 | M | CH₂C≡CH | H | NO₂ | OCH₃ |
| 523 | M | CH₂C≡CH | H | NO₂ | Cl |
| 524 | M | CH₂CH(CH₃)₂ | H | NO₂ | SC₂H₅ |
| 525 | M | CH₂CH(CH₃)₂ | H | NO₂ | N(CH₃)₂ |
| 526 | M | CH₂CH(CH₃)₂ | H | NO₂ | OCH₃ |
| 527 | M | CH₂CH(CH₃)₂ | H | NO₂ | Cl |
| 528 | M | 4-OCH₃-C₆H₄-CH₂CH₂- | H | NO₂ | SC₂H₅ |
| 529 | M | 4-OCH₃-C₆H₄-CH₂CH₂- | H | NO₂ | N(CH₃)₂ |
| 530 | M | 4-OCH₃-C₆H₄-CH₂CH₂- | H | NO₂ | OCH₃ |
| 531 | M | 4-OCH₃-C₆H₄-CH₂CH₂- | H | NO₂ | Cl |
| 532 | B* | CH₂CN | H | NO₂ | SC₂H₅ |
| 533 | B* | CH₂CN | H | NO₂ | N(CH₃)₂ |
| 534 | B* | CH₂CN | H | NO₂ | OCH₃ |
| 535 | B* | CH₂CN | H | NO₂ | Cl |
| 536 | B* | CH₂C≡CH | H | NO₂ | SC₂H₅ |
| 537 | B* | CH₂C≡CH | H | NO₂ | N(CH₃)₂ |
| 538 | B* | CH₂C≡CH | H | NO₂ | OCH₃ |
| 539 | B* | CH₂C≡CH | H | NO₂ | Cl |
| 540 | B* | CH₂CH(CH₃)₂ | H | NO₂ | SC₂H₅ |
| 541 | B* | CH₂CH(CH₃)₂ | H | NO₂ | N(CH₃)₂ |
| 542 | B* | CH₂CH(CH₃)₂ | H | NO₂ | OCH₃ |

TABLE 1-continued

| | | | | | |
|---|---|---|---|---|---|
| 543 | B* | CH$_2$CH(CH$_3$)$_2$ | H | NO$_2$ | Cl |
| 544 | B* | 4-OCH$_3$-benzyl (with ethyl) | H | NO$_2$ | SC$_2$H$_5$ |
| 545 | B* | 4-OCH$_3$-benzyl (with ethyl) | H | NO$_2$ | N(CH$_3$)$_2$ |
| 546 | B* | 4-OCH$_3$-benzyl (with ethyl) | H | NO$_2$ | OCH$_3$ |
| 547 | B* | 4-OCH$_3$-benzyl (with ethyl) | H | NO$_2$ | Cl |

*R$^3$ is Cl
**R$^1$, R$^2$ and R$^4$ are hydrogen and R$^3$ is chlorine

The following table sets forth physical characterizing data for certain compounds of formula I of the present invention:

TABLE 2

Insecticidal N,N-Di(heteroarylalkyl)amine Derivatives
Compound Characterization

| | Molecular Formula | Melting Point (° C.) of Solids Or Physical State |
|---|---|---|
| 1 | C$_{16}$H$_{18}$ClN$_5$O$_2$S | SYRUP |
| 4 | C$_{16}$H$_{19}$ClN$_6$O$_2$ | OIL |
| 8 | C$_{14}$H$_{13}$Cl$_2$N$_5$O$_2$ | SOLID |
| 18 | C$_{15}$H$_{13}$Cl$_2$N$_5$ | SOLID |
| 31 | C$_{17}$H$_{19}$ClN$_4$O$_2$S | OIL |
| 34 | C$_{17}$H$_{20}$ClN$_5$O$_2$ | OIL |
| 38 | C$_{15}$H$_{14}$Cl$_2$N$_4$O$_2$ | OIL |
| 48 | C$_{16}$H$_{14}$Cl$_2$N$_4$ | SOLID |
| 91 | C$_{19}$H$_{27}$ClN$_4$O$_2$S | OIL |
| 94 | C$_{19}$H$_{28}$ClN$_5$O$_2$ | OIL |
| 98 | C$_{17}$H$_{22}$Cl$_2$N$_4$O$_2$ | OIL |
| 121 | C$_{18}$H$_{25}$ClN$_4$O$_2$S | OIL |
| 128 | C$_{16}$H$_{20}$Cl$_2$N$_4$O$_2$ | OIL |
| 151 | C$_{21}$H$_{29}$ClN$_4$O$_2$S | OIL |
| 158 | C$_{19}$H$_{24}$Cl$_2$N$_4$O$_2$ | OIL |
| 188 | C$_{20}$H$_{20}$Cl$_2$N$_4$O$_3$ | SYRUP |
| 214 | C$_{21}$H$_{23}$Cl$_2$N$_5$O$_2$ | SYRUP |
| 241 | C$_{17}$H$_{23}$ClN$_4$O$_2$S | OIL |
| 242 | C$_{22}$H$_{25}$ClN$_4$O$_3$S | SYRUP |
| 243 | C$_{22}$H$_{22}$Cl$_2$N$_4$O$_5$ | 99-103 |
| 244 | C$_{13}$H$_{14}$Cl$_2$N$_4$O$_2$ | OIL |
| 245 | C$_{15}$H$_{19}$ClN$_4$O$_2$S | OIL |
| 246 | C$_{15}$H$_{15}$Cl$_2$N$_5$O$_2$ | SOLID |
| 247 | C$_{16}$H$_{16}$Cl$_2$N$_4$O$_2$ | OIL |
| 248 | C$_{15}$H$_{18}$Cl$_2$N$_4$O$_2$ | OIL |
| 249 | C$_{16}$H$_{18}$Cl$_2$N$_4$O$_2$ | OIL |
| 250 | C$_{17}$H$_{22}$Cl$_2$N$_4$O$_4$ | OIL |
| 251 | C$_{18}$H$_{23}$ClN$_4$O$_2$S | OIL |
| 252 | C$_{18}$H$_{24}$ClN$_5$O$_2$ | OIL |
| 253 | C$_{19}$H$_{27}$ClN$_4$O$_4$S | OIL |
| 254 | C$_{17}$H$_{23}$ClN$_4$O$_2$S | OIL |
| 255 | C$_{16}$H$_{20}$Cl$_2$N$_4$O$_3$ | OIL |
| 256 | C$_{19}$H$_{18}$Br$_2$ClN$_5$O$_3$ | OIL |
| 257 | C$_{13}$H$_{11}$Br$_2$ClN$_6$O$_2$ | 133-136 |
| 258 | C$_{14}$H$_{12}$Br$_2$ClN$_5$O$_2$ | OIL |
| 259 | C$_{16}$H$_{20}$Br$_2$ClN$_5$O$_2$ | OIL |
| 260 | C$_{12}$H$_{12}$Br$_2$ClN$_5$O$_2$ | OIL |
| 277 | C$_{18}$H$_{16}$Cl$_2$N$_6$O$_4$ | STICKY SOLID |
| 278 | C$_{18}$H$_{16}$Cl$_3$N$_5$O$_2$ | 114-116 |
| 279 | C$_{18}$H$_{16}$Cl$_3$N$_5$O$_2$ | STICKY SOLID |
| 280 | C$_{12}$H$_{13}$Cl$_2$N$_5$O$_2$ | OIL |
| 281 | C$_{12}$H$_{13}$Cl$_2$N$_5$O$_2$ | OIL |
| 282 | C$_{14}$H$_{13}$ClN$_6$O$_4$ | STICKY SOLID |
| 283 | C$_{14}$H$_{13}$Cl$_2$N$_5$O$_2$ | OIL |
| 284 | C$_{13}$H$_{12}$ClN$_7$O$_4$ | 110-113 |
| 285 | C$_{13}$H$_{12}$Cl$_2$N$_6$O$_2$ | 93-97 |
| 289 | C$_{13}$H$_{12}$Cl$_2$N$_6$O$_2$ | 108-112 |
| 293 | C$_{14}$H$_{13}$Cl$_2$N$_5$O$_2$ | 55-57 |
| 302 | C$_{16}$H$_{26}$ClN$_3$O$_3$ | OIL |
| 303 | C$_{18}$H$_{31}$N$_3$O$_3$S | OIL |
| 304 | C$_{13}$H$_{16}$Cl$_2$N$_4$O$_3$S | OIL |
| 305 | C$_{14}$H$_{16}$Cl$_2$N$_4$O$_2$S | OIL |
| 329 | C$_{13}$H$_{12}$Cl$_2$N$_4$O$_2$S | OIL |
| 409 | C$_{16}$H$_{16}$Cl$_2$N$_4$O$_2$ | OIL |
| 418 | C$_{17}$H$_{20}$Cl$_2$N$_4$O$_2$ | OIL |
| 419 | C$_{16}$H$_{20}$Cl$_2$N$_4$O$_3$ | OIL |

Candidate insecticides were evaluated for insecticidal activity by observing mortality in a population of cotton aphid (*Aphis gossypii*) on treated cotton plants when compared to like populations of cotton aphid on untreated plants. These tests were conducted in the following manner:

For each rate of application of test compound, two seven-to-ten days old cotton seedlings (*Gossypium hirsutium*) grown in 7.6 cm diameter pots were selected for the test. Each test plant was infested with about 120 adult cotton aphids by placing onto each test plant cuttings of leaves from cotton plants grown in a cotton aphid colony. Once infested, the test plants were maintained for up to about 12 hours to allow complete translocation of the aphids onto the test plant. A solution comprising 1000 part per million (ppm) of each test compound was prepared by dissolving 10 milligrams of the test compound in 1 mL of acetone. Each solution was then diluted with 9 mL of a solution of 0.03 mL of polyoxyethylene(10) isooctylphenyl ether in 100 mL of water. About 2.5 mL of solution of each test compound was needed to spray each replicate of test plant (5 mL total for each test compound). If needed, the solution of 1000 ppm of test compound was serially diluted with a solution of 10% acetone and 300 ppm of polyoxyethylene(10) isooctylphenyl ether in water to provide solutions of each test compound for lower rates of application, for example, 300 ppm, 100 ppm, 30 ppm, or 10 ppm. Each replicate of test plant was sprayed with the solutions of test compound until run-off on both the upper and lower surfaces of the leaves. All the test plants were sprayed using a DeVilbus Atomizer Model 152 (Sunrise Medical, Carlsbad, Calif.) at a pressure of about 0.63-0.74 kilogram per square centimeter from a distance of about 30.5 centimeters from the test plants. For comparison purposes, a solution of 10% acetone and 300 ppm of polyoxyethylene(10) isooctylphenyl ether in water containing no test compound was also sprayed onto control test plants. Upon completion of spraying the solutions of test compound and the solution containing no test compound, the plants were allowed to dry. Upon completion of drying, the test and control plants were placed in a tray containing about 2.5 centimeters of water, where they were maintained in a growth chamber for 72 hours. After this time, each plant was assessed for percent mortality caused by the test compound when compared to the population of aphids that was infested onto the test plants prior to treatment with test compound. A test compound was designated as possessing insecticidal activity (SA) if there was 40% to 75% mortality of cotton aphid on plants sprayed with that compound. If there was 75% mortality or greater of the cotton aphid, a test compound was designated as being more insecticidally active (A). If there was 40% mortality or less of the cotton aphid, the test compound was termed as inactive (I).

An assessment of the insecticidal activity at selected rates of application from this test is provided in Tables 3 and 3A. The test compounds of formula I are identified by numbers that correspond to those in Table 1.

cotyledons and new true leaf growth, leaving the oldest two true leaves. To infest, two seven-to-ten day old cotton plants, grown in a cotton aphid colony were uprooted and lodged in the apex of the stem where the stems of the two true leaves meet with the main stem. Once infested, the test plants were maintained for up to about 12 hours to allow complete translocation of the aphids onto the leaves of the test plant. The wells of clear 128-well trays (CD-International, Pittman, N.J.) were filled with 1 mL of a warm, aqueous 3% agar solution and allowed to cool to ambient temperature. The aphid infested cotton leaves were removed from the plants and placed bottom side up on a cutting platform. Circular discs were cut from the infested leaves and placed bottom side up onto the cooled agar gel, one disc per well. Each leaf disc was visually inspected to assure that a minimum of 10 live aphids were present. A 50 mM stock solution of the test compound was prepared by dissolving the appropriate amount of the test compound in DMSO. A solution comprising 1000 part per million (ppm) of each test compound was prepared by dissolving 10 µl of the stock solution in 140 µl of an aqueous 0.003% Kinetic® (a nonionic wetter/spreader/penetrant adjuvant) solution. If needed, the solution of 1000 ppm of test compound was serially diluted with a solution of 66 mL of DMSO and 30 µl of Kinetic® in 934 mL of water (diluting solution) to provide solutions of each test compound for lower rates of application, for example, 300 ppm, 100 ppm, 30 ppm, or 10 ppm. Each replicate test plant disc was sprayed with 10 µl of the test solution at about 8 psi for 1 second. For comparison purposes, an aqueous solution of 0.003% Kinetic® containing no test compound and the diluting solution containing no test compound were also sprayed onto test plant discs. Upon completion of spraying the solutions of test compound and the solutions containing no test compound, the plant discs were allowed to dry. Upon completion of drying, the test trays were covered with a plastic film.

TABLE 3

The following Compounds of The Present Invention Reduced the Population of Cotton Aphid by At Least 75% when Applied at an Application Rate of 300 ppm or Less

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|---|
| 1 | 4 | 31 | 34 | 38 | 91 | 94 | 98 | 121 | 128 |
| 188 | 214 | 241 | 242 | 244 | 245 | 247 | 248 | 249 | 250 |
| 251 | 252 | 253 | 254 | 255 | 281 | 304 | 305 | 329 | 409 |
| 418 | 419 | | | | | | | | |

TABLE 3A

The following Compounds of The Present Invention Reduced the Population of Cotton Aphid by 40% to 75% when Applied at an Application Rate of 300 ppm or Less

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|---|
| 8 | 151 | 260 | 277 | 279 | 293 | 302 | | | |

Candidate insecticides were also evaluated for cotton aphid insecticidal activity by observing mortality in a population of cotton aphid (*Aphis gossypii*) on treated cotton plant leaf discs when compared to like populations of cotton aphid on untreated plant leaf discs. These tests were conducted in the following manner:

Three week to one month-old cotton plants (*Gossypium hirsutium*) were prepared for infesting by cutting off the Three slits were made in the film over each well to allow air into each well. The test trays were placed in a biochamber (25° C., 16 hours light, 8 hours of dark and 35-40% relative humidity) for three days. After this time, each plant disc was assessed for percent mortality caused by the test compound when compared to the population of aphids that was infested onto the test plant discs containing no test compound. A test compound was designated as possessing insecticidal activity (SA) if there was 40% to 75% mortality of cotton aphid on plants sprayed with that compound. If there was 75% mortality or greater of the cotton aphid, a test compound was designated as being more insecticidally active (A). If there was 40% mortality or less of the cotton aphid, the test compound was termed as inactive (I).

An assessment of the insecticidal activity at selected rates of application from this test is provided in Table 3B. The test compounds of formula I are identified by numbers that correspond to those in Table 1.

TABLE 3B

The following Compounds of The Present Invention Reduced the Population of Cotton Aphid on Treated Leaf Disks by 40% to 100% when Applied at an Application Rate of 300 ppm or Less

| Cmpd. No. | Cmpd. No. | Cmpd. No. | Cmpd. No. |
| --- | --- | --- | --- |
| 158 | 246 | 282 | 285 |

Candidate insecticides were evaluated for activity against the tobacco budworm (*Heliothis virescens* [Fabricius]) in a surface-treated diet test.

In this test one mL of molten (65-70° C.) wheat germ-based artificial diet was pipetted into each well of a four by six (24 well) multi-well plate (ID# 430345-15.5 mm dia. X 17.6 mm deep; Corning Costar Corp., One Alewife Center, Cambridge, Mass. 02140). The diet was allowed to cool to ambient temperature before treatment with candidate insecticide.

For a determination of insecticidal activity, solutions of the candidate insecticides were prepared for testing using a Packard 204DT Multiprobe Robotic System (Packard Instrument Company, 800 Research Parkway, Meriden, Conn. 06450), in which the robot first diluted a standard 50 millimolar DMSO solution of candidate insecticide with a 1:1 water/acetone solution (V/V) in a ratio of 1:7 stock solution to water/acetone. The robot subsequently pipetted 40 microliters of the so-prepared solution onto the surface of the diet in each of three wells in the 24 multi-well plate. The process was repeated with solutions of seven other candidate insecticides. Once treated, the contents of the multi-well plate were allowed to dry, leaving 0.25 millimoles of candidate insecticide on the surface of the diet, or a concentration of 0.25 millimolar. Appropriate untreated controls containing only DMSO on the diet surface were also included in this test.

For evaluations of the insecticidal activity of a candidate insecticide at varying rates of application, the test was established as described above using sub-multiples of the standard 50 millimolar DMSO solution of candidate insecticide. For example, the standard 50 millimolar solution was diluted by the robot with DMSO to give 5, 0.5, 0.25, 0.05, 0.005, 0.0005 millimolar, or more dilute solutions of the candidate insecticide. In these evaluations there were six replicates of each rate of application placed on the surface of the diet in the 24 multi-well plate, for a total of four rates of application of candidate insecticide in each plate.

In each well of the test plate was placed one second instar tobacco budworm larvae, each weighing approximately five milligrams. After the larvae were placed in each well, the plate was sealed with clear polyfilm adhesive tape. The tape over each well was perforated to ensure an adequate air supply. The plates were then held in a growth chamber at 25° C. and 60% relative humidity for five days (light 14 hours/day). After the five-day exposure period insecticidal activity for each rate of application of candidate insecticide was assessed for insecticidal activity. A test compound was designated as possessing insecticidal activity (SA) if there was 40% to 75% mortality of tobacco budworm on diet treated with that compound. If there was 75% mortality or greater of the tobacco budworm, a test compound was designated as being more insecticidally active (A). If there was 40% mortality or less of the tobacco budworm, the test compound was termed as inactive (I).

Insecticidal activity data at selected rates of application from this test are provided in Table 4. The test compounds of formula I are identified by numbers that correspond to those in Table 1.

TABLE 4

The Following N,N-di(heteroarylalkyl)amine Derivatives Reduced the Population of Tobacco Budworm (*Heliothis virescens* [Fabricius]) When Applied to the Surface of the Diet by 75% or more

| Cmpd. No. | Cmpd. No. | Cmpd. No. | Cmpd. No. |
| --- | --- | --- | --- |
| 30 | 214 | 244 | 245 |
| 251 | | | |

Concentration of the candidate insecticide on the surface of the diet is 0.25 millimolar.

Candidate insecticides were evaluated for insecticidal activity by observing mortality in a population of silverleaf whitefly (*Bemisia argentifolii*) on treated cotton plant cotyledons when compared to like populations of silverleaf whitefly on untreated plant cotyledons. These tests were conducted in the following manner:

For each rate of application of test compound, two four to six days old cotton seedlings (*Gossypium hirsutium*) grown in 3-inch diameter pots were selected for the test. Each test plant was sprayed with a test solution comprising 300 part per million (ppm), or less, of each test compound prepared by dissolving 12 milligrams of the test compound in 4 mL of acetone. Each solution was then diluted with 36 mL of a surfactant and water solution prepared by dissolving 0.03 gm of Triton X-100® surfactant in 100 mL of distilled water, providing a stock test solution of 300 ppm. About 2.5 mL of solution of each test compound was needed to spray each replicate of test plant (5 mL total for each test compound). If needed, the solution of 300 ppm of test compound was diluted with a solution of 10% acetone and 300 ppm of Triton X-100® surfactant in water to provide solutions of each test compound for lower rates of application, for example, 100 ppm, 30 ppm, or 10 ppm. Each replicate of test plant was sprayed with the solutions of test compound until run-off on both the upper and lower surfaces of the leaves. All the test plants were sprayed using a DeVilbus Atomizer Model 152 (Sunrise Medical, Carlsbad, Calif.) at a pressure of about 0.63-0.74 kilogram per square centimeter from a distance of about 30.5 centimeters from the test plants. Upon completion of spraying the solutions of test compound and the solution containing no test compound, the plants were allowed to dry. Upon completion of drying, the test plants were excised at the soil surface and placed in a 1 ounce plastic cup containing a 2.5 cm filter paper moistened with 50 microliters of distilled water. Whiteflies (25-50) were added to each cup and a lid was placed on each. The test cups were maintained in a growth chamber for 72 hours at 70% relative humidity (light 12 hours/day). After this time, each test was assessed for percent mortality caused by the test compound when compared to the population of whiteflies that were infested onto the test plants. A test compound was designated as possessing insecticidal activity (SA) if there was 40% to 75% mortality of cotton aphid on plants sprayed with that compound. If there was 75% mortality or greater of the cotton aphid, a test compound was designated as being more insecticidally active (A). If there was 40% mortality or less of the cotton aphid, the test compound was termed as inactive (I).

An assessment of the insecticidal activity at selected rates of application from this test is provided in Table 5. The test compounds of formula I are identified by numbers that correspond to those in Table 1.

TABLE 5

The following Compounds of The Present Invention Reduced the Population of Silverleaf Whitefly (*Bemisia argentifolii*) by at Least 75% when Applied at an Application Rate of 300 ppm or Less

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|---|
| 91 | 94 | 98 | 121 | 128 | 248 | 249 | 250 | 252 | 254 |
| 304 | 305 | 329 | | | | | | | |

Candidate insecticides were evaluated for insecticidal activity by observing mortality in a population of tarnished plant bug nymphs (*Lygus lineolaris*) on treated broccoli plant leaves when compared to like populations of tarnished plant bug on untreated plant leaves. These tests were conducted in the following manner:

For each rate of application of test compound, four ten to fifteen days old broccoli seedlings (*Brassica oleracea*) grown in 3-inch diameter pots were selected for the test. Each test plant was sprayed with a test solution comprising 300 part per million (ppm), or less, of each test compound prepared by dissolving 12 milligrams of the test compound in 4 mL of acetone. Each solution was then diluted with 36 mL of a surfactant and water solution prepared by dissolving 0.03 gm of Triton X-100® surfactant in 100 mL of distilled water, providing a stock test solution of 300 ppm. About 2.5 mL of solution of each test compound was needed to spray each replicate of test plant (10 mL total for each test compound). If needed, the solution of 300 ppm of test compound was diluted with a solution of 10% acetone and 300 ppm of Triton X-1000 surfactant in water to provide solutions of each test compound for lower rates of application, for example, 100 ppm, 30 ppm, or 10 ppm. Each replicate of test plant was sprayed with the solutions of test compound until run-off on both the upper and lower surfaces of the leaves. All the test plants were sprayed using a DeVilbus Atomizer Model 152 (Sunrise Medical, Carlsbad, Calif.) at a pressure of about 0.63-0.74 kilogram per square centimeter from a distance of about 30.5 centimeters from the test plants. Upon completion of spraying the solutions of test compound and the solution containing no test compound, the plants were allowed to dry. Upon completion of drying, the treated foliage was removed and two leaves were placed into an 8 ounce unwaxed paper cup which contained a one inch piece of cut cotton wick, moistened by soaking for five seconds with distilled water. Four late second to early third instar tarnished plant bug nymphs were placed into each cup and a lid was placed on each. The test cups were maintained in a growth chamber for 72 hours at 70% relative humidity (light 12 hours/day). After this time, each test was assessed for percent mortality caused by the test compound when compared to the population of tarnished plant bug nymphs that were infested onto the test plant leaves. A test compound was designated as possessing insecticidal activity (SA) if there was 40% to 75% mortality of cotton aphid on plants sprayed with that compound. If there was 75% mortality or greater of the cotton aphid, a test compound was designated as being more insecticidally active (A). If there was 40% mortality or less of the cotton aphid, the test compound was termed as inactive (I).

An assessment of the insecticidal activity at selected rates of application from this test is provided in Table 6. The test compounds of formula I are identified by numbers that correspond to those in Table 1.

TABLE 6

The following Compounds of The Present Invention Reduced the Population of Tarnished Leaf Bug Nymphs (*Lygus lineolaris*) between 40% and 100% when Applied at an Application Rate of 300 ppm or Less

| Cmpd. No. | Cmpd. No. | Cmpd. No. | Cmpd. No. | Cmpd. No. | Cmpd. No. | Cmpd. No. | Cmpd. No. | Cmpd. No. | Cmpd. No. |
|---|---|---|---|---|---|---|---|---|---|
| 94 | 121 | 128 | 249 | 250 | 251 | 252 | 254 | 329 | 409 |

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of formula I

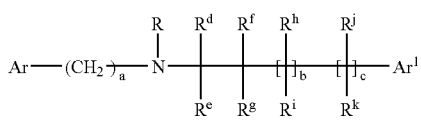

wherein
Ar is

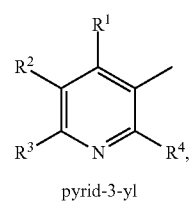

pyrid-3-yl where

R¹, R², R³, and R⁴ are independently selected from hydrogen, halogen, alkyl, alkoxy, haloalkyl, haloalkoxy and haloalkylsulfonyl;

Ar¹ is

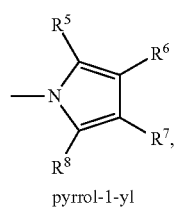

pyrrol-1-yl a is an integer selected from 0 or 1;

R is selected from alkyl, haloalkyl, alkoxyalkyl, alkoxyalkoxyalkyl, cycloalkylalkyl, formyl, alkylcarbonyl, alkoxycarbonyl, alkylsulfonyl, dialkylphosphonato, —(CH$_2$)$_m$C≡N, —(CH$_2$)$_m$—CR$^9$=CR$^{10}$R$^{11}$, —(CH$_2$)$_m$—C≡CR$^{12}$, and

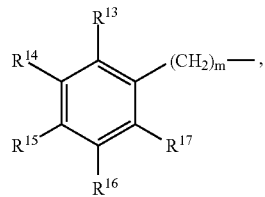

where m is an integer selected from 1 or 2;

R⁹, R¹⁰ and R¹¹ are independently selected from hydrogen, halogen, alkyl and aryl;

R¹² is selected from hydrogen, alkyl, and

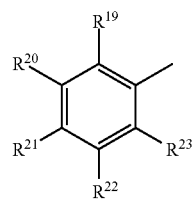

where

R¹⁹, R²⁰, R²¹, R²², an R²³ are independently selected from hydrogen, halogen, alkyl, haloalkyl, alkoxy, and haloalkoxy;

R¹³, R¹⁴, R¹⁵, R¹⁶, and R¹⁷ are independently selected from hydrogen, halogen, alkyl, haloalkyl, alkoxy, haloalkoxy, alkoxyiminoalkyl, cyano, nitro, aryl, and aryloxy;

R$^d$, R$^e$, R$^f$ and R$^g$ are independently selected from hydrogen and alkyl;

b and c are integers independently selected from 0 or 1;

R$^h$, R$^i$, R$^j$ and R$^k$ are independently selected from hydrogen and alkyl;

R⁵ and R⁶ are independently selected from hydrogen, halogen, nitro, alkyl, alkoxy, alkenyloxy, alkynyloxy, haloalkyl, haloalkoxy, alkylthio, alkenylthio, alkynylthio, haloalkylthio, alkylsulfoxy, alkylsulfinyl, alkylsulfonyl, haloalkylsulfonyl, alkylamino, dialkylamino, hydroxycarbonyl and alkoxycarbonyl;

R⁷ is selected from halogen, trifluoromethyl, cyano, nitro, formyl, hydroxycarbonyl, alkoxycarbonyl, aryloxycarbonyl, alkoxysulfonyl and alkoxysulfinyl;

R⁸ is selected from halogen, nitro, alkoxy, alkenyloxy, alkynyloxy, haloalkoxy, alkylthio, alkenylthio, alkynylthio, haloalkylthio, alkylsulfoxy, alkylsulfinyl, alkylsulfonyl, haloalkylsulfonyl, alkylamino and dialkylamino;

or an agriculturally acceptable salt thereof.

2. A compound of claim 1, wherein b and c are 0.

3. A compound of claim 2, wherein Ar is pyrid-3-yl (A).

4. A compound of claim 3, wherein R⁷ is nitro.

5. A composition comprising an insecticidally effective amount of a compound of claim 1 in admixture with at least one agriculturally acceptable extender or adjuvant.

6. A compound of formula I

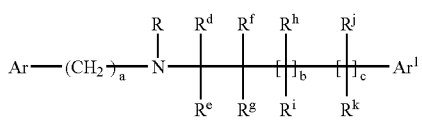

wherein

Ar is

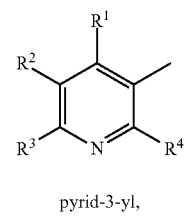

pyrid-3-yl, where

R¹, R², R³, and R⁴ are independently selected from hydrogen and halogen;

Ar¹ is

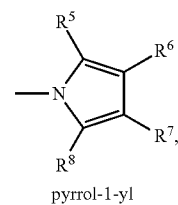

pyrrol-1-yl a is 1;

R is selected from alkyl, alkoxyalkyl, alkoxyalkoxyalkyl, cycloalkylalkyl, —(CH$_2$)$_m$C≡N, —(CH$_2$)$_m$—CR$^9$=CR$^{10}$R$^{11}$, —(CH$_2$)$_m$—C≡CR$^{12}$ and -continued

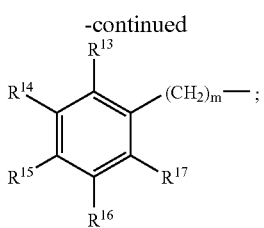

where
m is 1;
$R^9$, $R^{10}$, $R^{11}$ and $R^{12}$ are hydrogen;
$R^{13}$, $R^{14}$, $R^{15}$, $R^{16}$, and $R^{17}$ are independently selected from hydrogen, halogen and alkoxy;
$R^d$, $R^e$, $R^f$ and $R^g$ are hydrogen;
b and c are integers independently selected from 0 or 1;
$R^h$, $R^i$, $R^j$ and $R^k$ are hydrogen;

$R^5$ and $R^6$ are independently selected from hydrogen, halogen, alkyl, alkoxy, alkenyloxy, alkynyloxy, haloalkyl, haloalkoxy, alkylthio, alkenylthio, alkynylthio, haloalkylthio, alkylsulfoxy, alkylsulfinyl, alkylsulfonyl, haloalkylsulfonyl, alkylamino, dialkylamino, hydroxycarbonyl and alkoxycarbonyl;
$R^7$ is selected from trifluoromethyl, cyano and nitro;
$R^8$ is selected from halogen, nitro, alkoxy, alkylthio, alkylamino and dialkylamino;
or an agriculturally acceptable salt thereof.

7. A compound of claim 6, wherein b and c are 0.

8. A compound of claim 7, wherein Ar is pyrid-3-yl (A).

9. A compound of claim 8, wherein $R^7$ is nitro.

10. A composition comprising an insecticidally effective amount of a compound of claim 6 in admixture with at least one agriculturally acceptable extender or adjuvant.

* * * * *